United States Patent
Krumme et al.

(10) Patent No.: US 8,317,756 B2
(45) Date of Patent: Nov. 27, 2012

(54) SELF-CONTAINED PRESSURIZED INJECTION DEVICE

(75) Inventors: John F. Krumme, Woodside, CA (US); Leslie A. Field, Portola Valley, CA (US)

(73) Assignee: Nordson Corporation, Westlake, OH (US)

( * ) Notice: Subject to any disclaimer, the term of this patent is extended or adjusted under 35 U.S.C. 154(b) by 0 days.

(21) Appl. No.: 13/182,828

(22) Filed: Jul. 14, 2011

(65) Prior Publication Data

US 2011/0270186 A1    Nov. 3, 2011

Related U.S. Application Data

(62) Division of application No. 12/340,920, filed on Dec. 22, 2008, now Pat. No. 8,002,753.

(60) Provisional application No. 61/016,223, filed on Dec. 21, 2007.

(51) Int. Cl.
*A61M 5/00* (2006.01)
*A61M 37/00* (2006.01)
*A61M 5/178* (2006.01)

(52) U.S. Cl. .................. 604/207; 604/141; 604/186

(58) Field of Classification Search .............. 604/186, 604/140, 141, 207

See application file for complete search history.

(56) References Cited

U.S. PATENT DOCUMENTS

| | | | | |
|---|---|---|---|---|
| 6,264,629 | B1 * | 7/2001 | Landau | 604/68 |
| 6,537,246 | B1 * | 3/2003 | Unger et al. | 604/82 |
| 2003/0233070 | A1 * | 12/2003 | De La Serna et al. | 604/141 |

* cited by examiner

*Primary Examiner* — Nicholas Lucchesi
*Assistant Examiner* — Jenna Zhang
(74) *Attorney, Agent, or Firm* — Wood, Herron & Evans, L.L.P.

(57) ABSTRACT

An apparatus includes a medicament container and an actuator assembly coupled to a proximal end portion of the medicament container. A distal end portion of the medicament container is configured to be coupled to a needle. A piston is movably disposed within the medicament container such that the medicament container is divided into a first internal portion and a second internal portion, the first internal portion containing a medicament. The actuator assembly has a pressurized fluid container, a regulator and a bias member. The pressurized fluid container is configured to move relative to the medicament container between a first position and a second position. The regulator is configured to fluidically couple the pressurized fluid container and the second internal portion of the medicament container when the pressurized fluid container is in the second position. The bias member is configured to bias the pressurized fluid container in the first position.

20 Claims, 12 Drawing Sheets

SELF-CONTAINED PRESSURIZED INJECTION DEVICE

CROSS-REFERENCE TO RELATED APPLICATIONS

This application is a divisional of application Ser. No. 12/340,920, filed Dec. 22, 2008 (pending) which claims the benefit of U.S. Provisional Application Ser. No. 61/016,223, filed Dec. 21, 2007, the disclosures of which are incorporated herein by reference in their entirety.

BACKGROUND

Embodiments discussed herein relate generally to medical devices and methods, and more particularly to self-contained pressurized injection devices.

Known dermal fillers can be injected into a patient's body to augment soft tissue portions within the body. For example, some known filler compositions can be injected adjacent the urinary sphincter muscle to increase the volume of the tissue within the urinary tract to treat urinary incontinence. Known dermal fillers can also be injected into the skin to change the contour of and/or increase the volume of the skin. For example, known high viscosity compositions can be injected within facial skin to remove wrinkles, treat scars or the like.

Some known procedures for injecting dermal fillers include injecting the dermal filler using a standard syringe. In such procedures, the force and/or pressure required to convey the dermal filler from the syringe body through the needle can be generated manually by having the user manually depress a plunger into the syringe body. The force generated by manually depressing a plunger, however, can be sporadic, thus resulting in undesirable fluctuations in the flow of the dermal filler through the needle, which can result in the user injecting more or less dermal filler at a particular location within the body than is desired. Generating the injection force and/or pressure manually can also result in inconsistent results between different users. Moreover, in certain situations, the force generated by manually depressing a plunger can be insufficient to provide the desired flow rate of dermal filler. Additionally, because the total volume of dermal filler injected is a function of the length of travel of the plunger, it can be difficult to deliver a sufficient volume of dermal filler when injecting the dermal filler manually using a standard syringe. Moreover, generating the injection force and/or pressure manually can result in user fatigue and/or chronic health problems for the user, such as, for example arthritis.

Thus, a need exists for improved apparatus and methods for injecting dermal fillers into a body.

SUMMARY

Medical injectors and methods of injecting dermal fillers are described herein. In some embodiments, an apparatus includes a medicament container and an actuator assembly coupled to a proximal end portion of the medicament container. A distal end portion of the medicament container is configured to be coupled to a needle. A piston is movably disposed within the medicament container such that the medicament container is divided into a first internal portion and a second internal portion. The first internal portion is configured to contain a medicament. The actuator assembly has a pressurized fluid container, a regulator and a bias member. The pressurized fluid container is configured to move relative to the medicament container between a first position and a second position. The regulator is configured to fluidically couple the pressurized fluid container and the second internal portion of the medicament container when the pressurized fluid container is in the second position. The bias member is configured to bias the pressurized fluid container in the first position.

DETAILED DESCRIPTION

Figure 1:
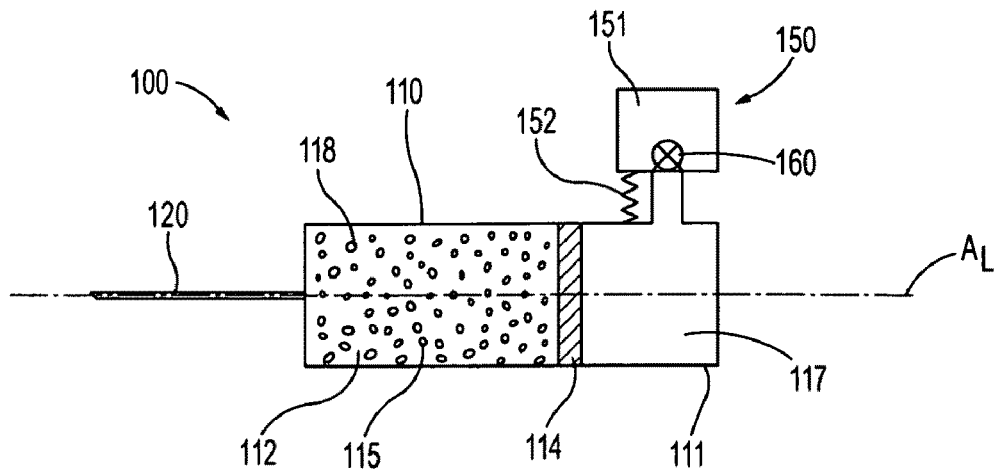
FIGS. 1 and 2 are schematic illustrations of a medical injector according to an embodiment in a first configuration and a second configuration, respectively.

In some embodiments, an apparatus includes a medicament container and an actuator assembly coupled to a proximal end portion of the medicament container. A distal end portion of the medicament container is configured to be coupled to a needle. A piston is movably disposed within the medicament container such that the medicament container is divided into a first internal portion and a second internal portion. The first internal portion is configured to contain a medicament, such as, for example a dermal filler. The actuator assembly has a pressurized fluid container, a regulator and a bias member. The pressurized fluid container, which can contain, for example, a fluid propellant, is configured to move relative to the medicament container between a first position and a second position. The regulator is configured to fluidically couple the pressurized fluid container and the second internal portion of the medicament container when the pressurized fluid container is in the second position. The bias member is configured to bias the pressurized fluid container in the first position.

In some embodiments, a medical injector can be actuated via a user's thumb (e.g., through a "syringe type" grip configuration") to non-manually inject a dermal filler. For example, in some such embodiments, a medical injector includes a medicament container, a pressurized fluid container coupled to a proximal end portion of the medicament container, and a regulator. A distal end portion of the medicament container is configured to be coupled to a needle (e.g., via a Luer fitting or the like). A central portion of the medicament container includes a finger grip configured to engage a first finger and a second finger of a user. A piston is movably disposed within the medicament container such that the medicament container is divided into a first internal portion and a second internal portion, the first internal portion containing a medicament. The pressurized fluid container is configured to be moved relative to the medicament container from a first position to a second position when the finger grip is engaged by the first finger and the second finger and when a proximal end of the pressurized fluid container is moved relative to the finger grip via a thumb of the user. The regulator is configured to fluidically couple the pressurized fluid container and the second internal portion of the medicament container when the pressurized fluid container is in the second position.

In some embodiments, a medical injector can regulate a flow of a medicament during an injection event by restricting a flow path between a medicament container and a needle. For example, in some embodiments, a medical injector includes a medicament container, a pressurized fluid container coupled to a proximal end portion of the medicament container, and a valve mechanism. A distal end portion of the medicament container is configured to be coupled to a needle. A piston is movably disposed within the medicament container such that the medicament container is divided into a first internal portion and a second internal portion, the first internal portion containing a medicament. The pressurized fluid container is configured to be selectively placed in fluid communication with the second internal portion of the medicament container. The valve mechanism is coupled to the distal end portion of the medicament container, and is configured to selectively restrict a flow path between the first internal portion of the medicament container and the needle. The valve mechanism is configured to be actuated via an actuator configured to move in a direction substantially normal to a longitudinal axis of the medicament container.

As used herein, the words "proximal" and "distal" refer to direction closer to and away from, respectively, an operator or user (e.g., surgeon, physician, nurse, technician, etc.) of the medical device. Thus, for example, the end of the medicament delivery device contacting the patient's body would be the distal end of the medicament delivery device, while the end opposite the distal end would be the proximal end of the medicament delivery device.

As used herein, the words "non-manual" or "non-manually" are used to describe an operation and/or an apparatus in which a source of energy and/or a force for carrying out the operation and/or a function of the apparatus is not directly produced by a human. For example, an apparatus for non-manually injecting a dermal filler can include any apparatus in which the force to inject the dermal filler is not directly produced by a human. Examples of a non-manual injection apparatus include an apparatus having a pressurized fluid source to provide the injection force, an apparatus having a spring to provide the injection force, and an apparatus having an electric motor to provide the injection force. An apparatus for non-manually injecting a dermal filler can include a manual actuator (e.g., an on/off switch, a push button, a foot pedal or the like) to initiate the non-manual injection.

Figure 2:
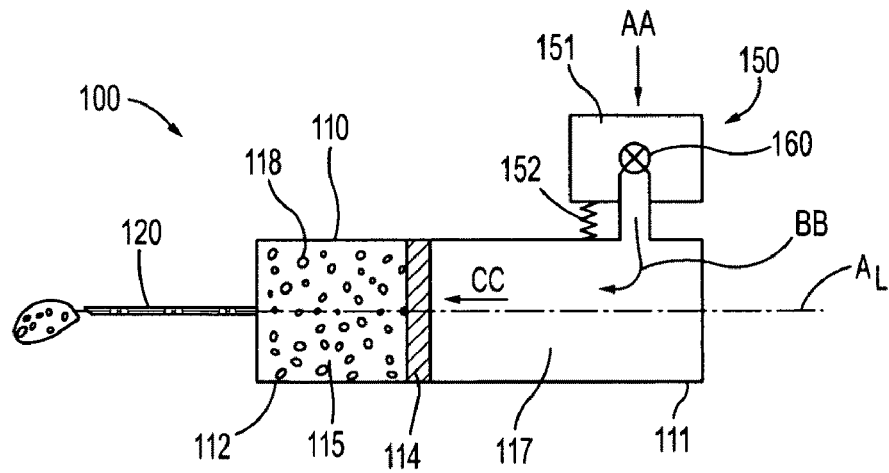

FIGS. 1 and 2 are schematic illustrations of a medical injector 100 according to an embodiment, in a first configuration and a second configuration, respectively. The medical injector 100 includes a medicament container 110, a needle 120 and an actuator assembly 150. The medicament container 110 has a proximal end portion 111 and a distal end portion 112, and defines a longitudinal axis $A_L$. The medicament container includes a piston 114 movably disposed therein such that the medicament container 110 is divided by the piston 114 into a first internal portion 115 and a second internal portion 117. In some embodiments, for example, the piston 114 can be disposed within the medicament container 110 such that the first internal portion 115 of the medicament container 110 is fluidically isolated from the second internal portion 117 of the medicament container 110.

The first internal portion 115 of the medicament container 110 is configured to contain a medicament 118 suitable for being injected into a patient's body. The medicament 118 can be any medicament of the types shown and described herein. For example, in some embodiments, the medicament 118 can include a dermal filler, a sub-dermal filler, a therapeutic substance for mesotherapy or the like. Moreover, the medicament 118 can be in any suitable state of matter (e.g., a liquid dermal filler, a paste-like dermal filler, a dermal filler including both a liquid component and a solid component, or the like).

The needle 120 is coupled to the distal end portion 112 of the medicament container 110 such that the needle 120 is in fluid communication with the first internal portion 115 of the medicament container 110. The needle 120 can be coupled to the medicament container 110 by any suitable mechanism. For example, in some embodiments, the needle 120 can be coupled to the medicament container 110 by a Luer fitting that provides a substantially fluid-tight seal (i.e., a seal that that substantially prevents a liquid and/or a gas from passing therethrough) between the needle 120 and the medicament container 110. In some embodiments, the fluid-tight seal can be a hermetic seal (i.e., a seal that substantially prevents a gas from passing therethrough).

The actuator assembly 150, which is configured to actuate the medical injector to inject the medicament 118, is coupled to the proximal end portion 111 of the medicament container 110. The actuator assembly 150 includes a pressurized fluid container 151, a bias member 152 and a regulator 160. The pressurized fluid container 151 contains a pressurized fluid that can be conveyed into the second internal portion 117 of the medicament container 110 to move the piston 114 within the medicament container 110, as described in more detail herein. In this manner, the pressurized fluid container 151 provides a source of energy that can non-manually move the piston 114 to cause injection of the medicament 118. The pressurized fluid contained within the pressurized fluid container 151 can be any pressurized fluid (e.g., pressurized gas and/or pressurized liquid) of the types described herein. For example, in some embodiments, the pressurized fluid container 151 can contain a propellant including fluorinated alkanes (e.g., 1,1,1,2-tetrafluoroethane (HFA 134a) and 1,1,1,2,3,3,3-heptafluoropropane (HFA 227)).

As shown in FIGS. 1 and 2, the pressurized fluid container 151 is configured to move relative to the medicament container 110 between a first position and a second position, as shown by the arrow AA in FIG. 2. Similarly stated, the medical injector 100 can be moved between a first configuration (corresponding to the first position of the pressurized fluid container 151) and a second configuration (corresponding to the second position of the pressurized fluid container 151). When the pressurized fluid container 151 is in the first position, the regulator 160 fluidically isolates the pressurized fluid container 151 from the second internal portion 117 of the medicament container 110. In this manner, when the pressurized fluid container 151 is in the first position, the piston 114 remains in a substantially fixed position within the medicament container 110.

When the pressurized fluid container 151 is in the second position, the regulator 160 fluidically couples the pressurized fluid container 151 and the second internal portion 117 of the medicament container 110. Thus, when the pressurized fluid container 151 is in the second position, the pressurized fluid from the pressurized fluid container 151 can flow into the second internal portion 117 of the medicament container 110, as shown by the arrow BB in FIG. 2. The pressurized fluid within the second internal portion 117 of the medicament container 110 exerts a force on the piston 114, causing the piston 114 to move within the medicament container 110 as shown by the arrow CC. When the piston 114 moves within the medicament container 110, the medicament 118 is conveyed from the first internal portion 115 of the medicament container 110 via the needle 120. Said another way, a user (or operator) can non-manually inject the medicament 118 into a body by actuating the medical injector 100 to cause the piston 114 to move distally within the medicament container 110.

The bias member 152 is configured to bias the pressurized fluid container 151 in the first position. Similarly stated, the bias member 152 is configured to maintain the pressurized fluid container 151 in the first position absent any external force (e.g., the user depressing the pressurized fluid container 151) such that the pressurized fluid container 151 is fluidically isolated from the second internal portion 117 of the medicament container 110. In this manner, the first configuration (i.e., the "non-actuated" configuration) is the nominal configuration of the medical injector 100.

Moreover, the arrangement of the bias member 152 allows the medical injector 100 to be toggled between the first configuration and the second configuration. Similarly stated, this arrangement allows a user to repeatedly and/or controllably move the pressurized fluid container 151 between the first position and the second position. Said another way, this arrangement allows the user to selectively couple and decouple the pressurized fluid container 151 and the medicament container 110. In this manner, for example, the flow rate of the dermal filler 118 from the medical injector 100 can be regulated to produce a discontinuous bead and/or set of beads of dermal filler 118 within the skin.

The bias member 152 can be any suitable mechanism for biasing the pressurized fluid container 151 in the first position. In some embodiments, the bias member 152 is a spring (e.g., a cantilever spring, a coil spring or the like). In other embodiments, the bias member 152 is an elastic member configured to produce a biasing force when deformed (e.g., when the pressurized fluid container 151 in the second position). In yet other embodiments, the bias member 152 can include a magnet to produce a biasing force.

The bias member 152 can be configured to produce any suitable biasing force urging the pressurized fluid container 151 in the first position. For example, in some embodiments, the bias member 152 can produce a force having a magnitude high enough to prevent inadvertent actuation of the medical injector 100 but low enough such that the user will not become fatigued when repeatedly actuating the medical injector 100. For example, in some embodiments, the bias member 152 can produce a force having a magnitude between approximately 0.45 N (1 lbf) and approximately 2.3 N (5 lbf).

In other embodiments, the bias member 152 can produce a force having a magnitude between approximately 0.9 N (2 lbf) and approximately 1.8 N (4 lbf). In some embodiments, the bias member 152 can be configured to produce a force having a magnitude that varies as a function of the distance through which the pressurized fluid container 151 moves relative to the medicament container 110. For example, in some embodiments, the bias member 152 can include a non-linear spring.

The regulator 160 can be any suitable mechanism for selectively placing the pressurized fluid container 151 in fluid communication with the second internal portion 117 of the medicament container 110. In some embodiments, for example, the regulator 160 can be an on/off valve having only two positions (e.g., corresponding to the first configuration and the second configuration). In other embodiments, the regulator 160 can regulate the flow rate of the pressurized fluid into the second internal portion 117 of the medicament container 110. By regulating of the flow rate of the pressurized fluid into the second internal portion 117 of the medicament container 110, the user can control the speed and/or distance through which the piston 114 moves within the medicament container 110. Similarly stated, by regulating of the flow rate of the pressurized fluid into the second internal portion 117 of the medicament container 110, the user can regulate the flow rate of the medicament 118 through the needle 120. For example, in some embodiments, the regulator 160 can regulate the flow rate of the pressurized fluid into the second internal portion 117 of the medicament container 110 as a function of the position of the pressurized fluid container 151 relative to the medicament container 110. In this manner, in some embodiments, the user can move the pressurized fluid container 151 relative to the medicament container 110 through any number of positions (e.g., between the first or closed position and the second or fully opened position) to regulate the flow rate of the pressurized fluid into the second internal portion 117 of the medicament container 110.

Because the dermal filler 118 is conveyed from the medicament container 110 via the needle 120 non-manually, the user is not burdened with producing the force used to cause the injection. Rather, the user can produce only the force used to move the pressurized fluid container 151 from the first position to the second position. In this manner, the operation of producing a force to inject the dermal filler 118 (which is performed non-manually by the pressurized fluid) is independent from the operation of actuating the medical injector. This arrangement can result in a repeatable, continuous and/or controlled injection of the dermal filler 118.

In contrast, some known medical injectors require the user to use the same hand to produce a force in a distal direction along a longitudinal axis of the medical injector to inject a dermal filler and move the needle along the longitudinal axis, for example, in an opposite (i.e., proximal) direction. In such instances, the injection of the dermal filler can be irregular, uncontrolled and/or discontinuous. Moreover, the disadvantage of such manual injection procedures can be exacerbated when injecting high viscosity dermal fillers, because, as described herein, the force to inject such dermal fillers can be in excess of approximately 4.5 N (10 lbf). For example, when injecting high viscosity dermal fillers using known medical injectors, it can be difficult for the user to maintain the force used to inject the dermal filler at the desired flow rate throughout the injection event. Thus, when injecting high viscosity dermal fillers using known medical injectors, the resulting bead of dermal filler can have undesirable spatial variability in its size and/or volume.

Although the pressurized fluid container 151 is shown as moving in a direction substantially normal to the longitudinal axis $A_L$ of the medicament container 110, in other embodiments, a pressurized fluid container can move in any suitable manner and/or direction. For example, in some embodiments, a pressurized fluid container can move in a direction non-normal to the longitudinal axis of a medicament container. In other embodiments, a pressurized fluid container can rotate relative to a medicament container.

Although the pressurized fluid container 151 is shown as being spaced apart from the medicament container 110 when in the second position (FIG. 2), in other embodiments, at least a portion of the pressurized fluid container 151 can be in contact with the medicament container 110 when in the first position and/or the second position.

Figure 3:
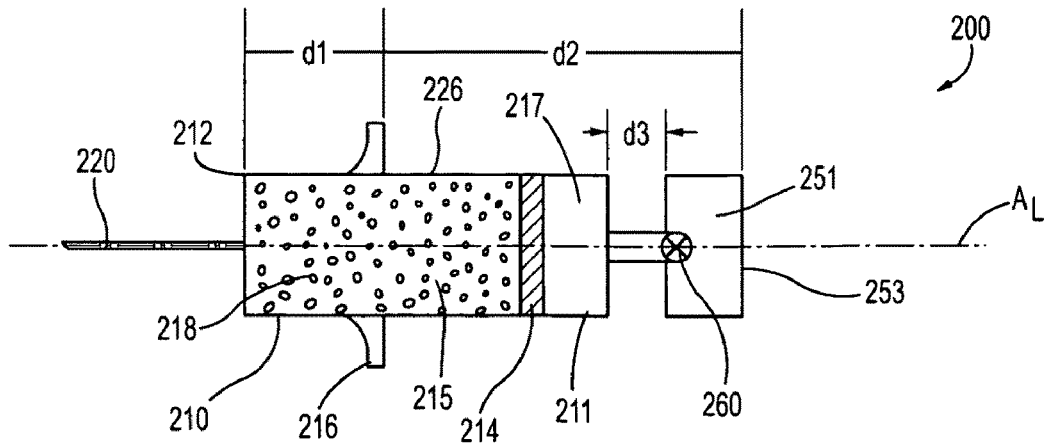
FIGS. 3 and 4 are schematic illustrations of a medical injector according to an embodiment in a first configuration and a second configuration, respectively.
Figure 4:
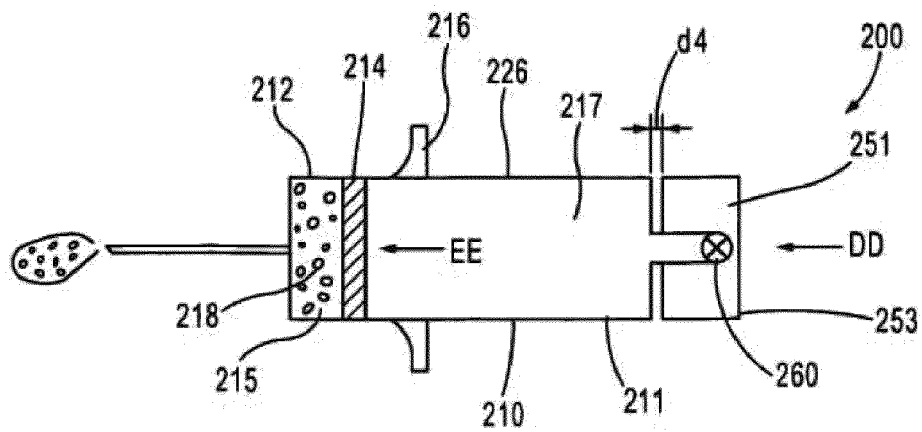

Although the pressurized fluid container 151 is shown and described as being offset from the longitudinal axis $A_L$ of the medicament container 110, in other embodiments, a pressurized fluid container can be coupled to a medicament container in any suitable manner. For example, in some embodiments, a medical injector can be configured to be actuated via a user's thumb (e.g., through a "syringe type" grip configuration") to non-manually inject a dermal filler. For example, FIGS. 3 and 4 are schematic illustrations of a medical injector 200 according to an embodiment, in a first configuration and a second configuration, respectively. The medical injector 200 includes a medicament container 210, a pressurized fluid container 251 and a regulator 260. The medicament container 210 has a proximal end portion 211, a distal end portion 212 and a central portion 226 therebetween, and defines a longitudinal axis $A_L$ (see e.g., FIG. 3). The medicament container includes a piston 214 movably disposed therein such that the medicament container 210 is divided by the piston 214 into a first internal portion 215 and a second internal portion 217. In some embodiments, for example, the piston 214 can be disposed within the medicament container 210 such that the first internal portion 215 of the medicament container 210 is fluidically isolated from the second internal portion 217 of the medicament container 210.

The first internal portion 215 of the medicament container 210 is configured to contain a medicament 218 suitable for being injected into a body. The medicament 218 can be any medicament of the types shown and described herein. For example, in some embodiments, the medicament 218 can include a dermal filler, a sub-dermal filler, a therapeutic substance for mesotherapy or the like. A needle 220 is coupled to the distal end portion 212 of the medicament container 210 such that the needle 220 is in fluid communication with the first internal portion 215 of the medicament container 210. In this manner, the medicament 218 can be conveyed from the first internal portion 215 of the medicament container 210 via the needle 220 during an injection event.

The central portion 226 of the medicament container 210 includes a finger grip 216. The finger grip 216 is configured to engage at least a first finger (e.g., an index finger) and a second finger (e.g., a middle finger) of the user. In this manner, a user can grasp the central portion 226 of the medicament container 210 to insert the needle 220 into the skin of a patient, to actuate the medical injector 200 and/or otherwise manipulate the medical injector 200. The finger grip 216 can have any suitable shape and/or contour for engaging and/or retaining at least the first finger and the second finger of the user. In some embodiments, for example, a finger grip can include an opening within which a portion of finger can be inserted.

As shown in FIG. 3, the finger grip 216 is spaced apart from the proximal end of the needle 220 by a distance d1. The distance d1 can be selected, for example, to provide a desired level of dexterity and/or control for the user when manipulating the medical injector 200. In some embodiments, for example, the distance d1 is less than approximately 25.4 mm (1 inch). In other embodiments, the distance d1 is less than approximately 12.7 mm (½ inch).

Similarly, the finger grip 216 is spaced apart from a proximal end 253 of the pressurized fluid container 251 by a distance d2. As described in more detail below, the proximal end 253 of the pressurized fluid container 251 is configured to receive a thumb of the user when the finger grip 216 is engaged by a finger or fingers of the user. Thus, distance d2 can be selected, for example, to provide a desired level of dexterity and/or control for the user when manipulating and/or actuating the medical injector 200. Said another way, the distance d2 is such that the medical injector 200 can fit within and/or be actuated by the user's hand. In some embodiments, for example, the distance d2 is less than approximately 101.6 mm (4 inches). In other embodiments, the distance d2 is less than approximately 76.2 mm (3 inches). In yet other embodiments, the distance d2 is between approximately 50.8 mm (2 inches) and approximately 101.6 mm (4 inches).

In some embodiments, the finger grip 216 can be monolithically constructed with the medicament container 210. In other embodiments, the finger grip 216 can be constructed separately from the medicament container 210 and later coupled to the medicament container 210. In some embodiments, for example, the finger grip 216 can include a sheath or covering configured to be disposed about and coupled to an outer surface of the medicament container 210. In this manner, the finger grip 216 can be coupled to a commercially-available medicament container (e.g., a commercially-available and/or prefilled syringe).

The pressurized fluid container 251 is movably coupled to the proximal end portion 211 of the medicament container 210. The pressurized fluid container 251 contains a pressurized fluid that can be conveyed into the second internal portion 217 of the medicament container 210 to move the piston 214 within the medicament container 210, as described in more detail herein. In this manner, the pressurized fluid container 251 provides a source of energy that can non-manually move the piston 214 to cause injection of the medicament 218. The pressurized fluid contained within the pressurized fluid container 251 can be any pressurized fluid of the types described herein. For example, in some embodiments, the pressurized fluid container 251 can contain a propellant including fluorinated alkanes (e.g., 2,1,1,2-tetrafluoroethane (HFA 234a) and 1,1,1,2,3,3,3-heptafluoropropane (HFA 227)).

As shown in FIGS. 3 and 4, the pressurized fluid container 251 is configured to move relative to the medicament container 210 between a first position and a second position, as shown by the arrow DD in FIG. 4. Similarly stated, the medical injector 200 can be moved between a first configuration (corresponding to the first position of the pressurized fluid container 251) and a second configuration (corresponding to the second position of the pressurized fluid container 251). When the pressurized fluid container 251 is in the first position, the distal end of the pressurized fluid container 251 is spaced apart from the medicament container 210 by a distance d3. When the pressurized fluid container 251 is in the first position, the regulator 260 fluidically isolates the pressurized fluid container 251 from the second internal portion 217 of the medicament container 210. In this manner, when the pressurized fluid container 251 is in the first position, the piston 214 remains in a substantially fixed position within the medicament container 210.

When the pressurized fluid container 251 is in the second position, the distal end of the pressurized fluid container 251 is spaced apart from the medicament container 210 by a distance d4. Moreover, when the pressurized fluid container 251 is in the second position, the regulator 260 fluidically couples the pressurized fluid container 251 and the second internal portion 217 of the medicament container 210. Thus, when the pressurized fluid container 251 is in the second position, the pressurized fluid from the pressurized fluid container 251 can flow into the second internal portion 217 of the medicament container 210. The pressurized fluid within the second internal portion 217 of the medicament container 210 exerts a force on the piston 214, causing the piston 214 to move within the medicament container 210 as shown by the arrow EE in FIG. 4. When the piston 214 moves within the medicament container 210, the medicament 218 is conveyed from the first internal portion 215 of the medicament container 210 via the needle 220.

The medical injector 200 can be moved from the first configuration (FIG. 3) to the second configuration (FIG. 4) when the finger grip 216 is engaged by the first finger and the second finger (not shown) of the user and the proximal end 253 of the pressurized fluid container 251 is moved relative to the finger grip 216 via a thumb (not shown) of the user. Similarly stated, the medical injector 200 is configured to be actuated in a manner similar to how a manual syringe is actuated.

When the medical injector 200 is moved from the first configuration to the second configuration, the pressurized fluid container 251 is moved relative to the medicament container 210 by the difference between the distance d3 and the distance d4 (i.e., the actuation stroke). In some embodiments, the actuation stroke is less than approximately 13 mm (approximately ½ inch). In other embodiments, the actuation stroke is less than approximately 6.4 mm (approximately ¼ inch). In yet other embodiments, the actuation stroke is less than approximately 3 mm (approximately ⅛ inch). Because the dermal filler 118 is conveyed from the medicament container 110 via the needle 120 non-manually, however, the distance through which the piston 214 moves within the medicament container 210 is independent from the actuation stroke. Thus, a length of travel of the piston 214, which is proportional to the amount of medicament 218 that can be injected, need not be limited based on a size of the user's hand. In this manner, the medical injector 200 can be configured to inject any suitable amount of medicament 218, (e.g., 1 to 2 cubic centimeters, 3 cubic centimeters, 4 cubic centimeters, 5 cubic centimeters or 10 cubic centimeters). In contrast, some known medical injectors that require the user to manually produce a force in a distal direction using a thumb are limited in how much medicament can be injected based on the size of the user's hand, the force required and/or the like.

The regulator 260 can be any suitable mechanism for selectively placing the pressurized fluid container 251 in fluid communication with the second internal portion 217 of the medicament container 210. In some embodiments, for example, the regulator 260 can be an on/off valve having only two positions (e.g., corresponding to the first configuration and the second configuration). In other embodiments, the regulator 260 can regulate the flow rate of the pressurized fluid into the second internal portion 217 of the medicament container 210, as described above.

Figure 5:
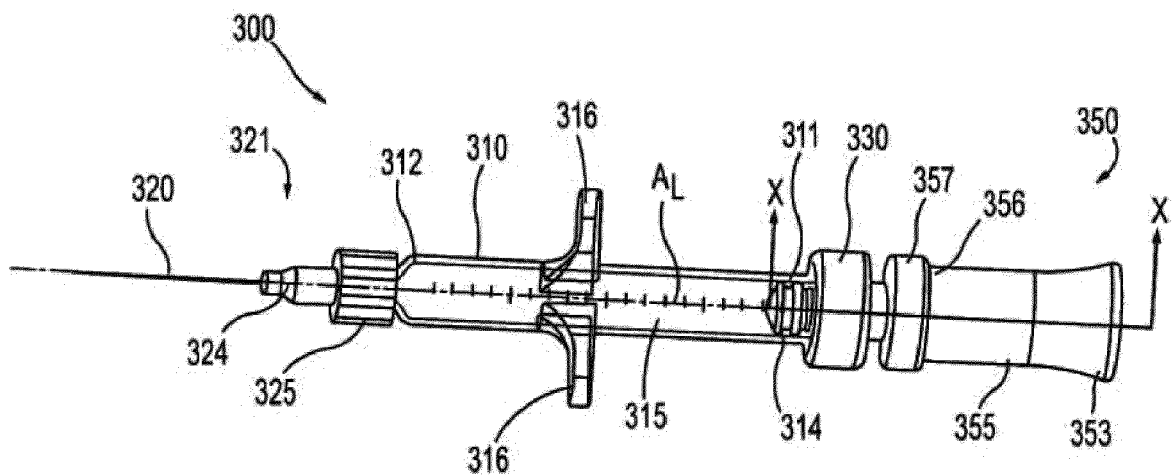
FIG. 5 is a perspective view of a medical injector including a self-contained source of pressurized fluid according to an embodiment.
Figure 6:
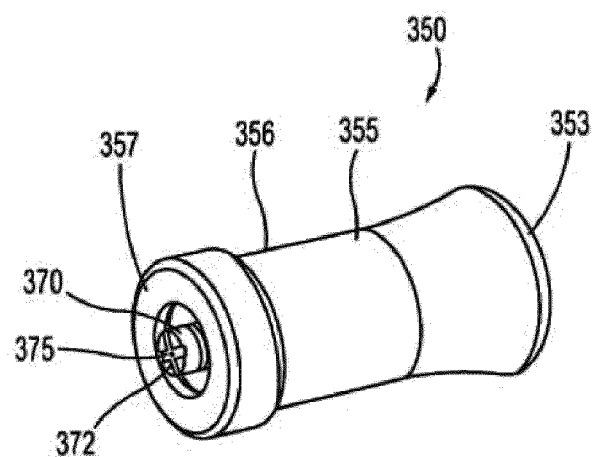
FIGS. 6 and 7 are a perspective view and an exploded view, respectively, of an actuator assembly of the medical injector shown in FIG. 5.

FIGS. 5-9 show a medical injector 300 according to an embodiment configured to non-manually inject a medicament using a pressurized fluid. As shown in FIG. 5, the medical injector 300 includes a medicament container 310, a needle assembly 321 and an actuator assembly 350. The medicament container 310 has a proximal end portion 311 and a distal end portion 312, and defines a longitudinal axis $A_L$. The medicament container includes a piston 314 movably disposed therein such that the medicament container 310 is divided by the piston 314 into a first internal portion 315 (see e.g., FIG. 5) and a second internal portion 317 (see FIGS. 8 and 9). The piston 314 is disposed within the medicament container 310 such that the first internal portion 315 of the medicament container 310 is fluidically isolated from the second internal portion 317 of the medicament container 310.

An outer surface of the medicament container 210 includes two protrusions 316 extending radially from the medicament container 310. The protrusions 316 are configured to engage at least a first finger (e.g., an index finger) and a second finger (e.g., a middle finger) of a user. In this manner, a user can grasp the medicament container 310 to insert the needle 320 into the skin of a patient, to actuate the medical injector 300 and/or otherwise manipulate the medical injector 300.

The first internal portion 315 of the medicament container 310 contains a medicament (not shown FIGS. 5-9) suitable for being injected into a body. The medicament can be any medicament of the types shown and described herein. For example, in some embodiments, the medicament can include a dermal filler, a sub-dermal filler, a therapeutic substance for mesotherapy or the like. Moreover, the medicament can be in any suitable state of matter (e.g., a liquid dermal filler, a paste-like dermal filler, a dermal filler including both a liquid component and a solid component, or the like).

The needle assembly 321 includes a needle 320 and a needle hub 324. The needle assembly 321 is coupled to the distal end portion 312 of the medicament container 310 via the coupler 325 such that the needle 320 is in fluid communication with the medicament container 310. Moreover, the coupler 325 couples the needle assembly 321 and the medicament container 310 such that the medicament does not leak from the interface between the medicament container 310 and the needle assembly 321 when the medicament is conveyed from the medicament container 310 via the needle 321. Said another way, the coupler 325 provides a substantially fluid-tight seal (i.e., a seal that that substantially prevents a liquid and/or a gas from passing therethrough) between the needle assembly 321 and the medicament container 310. In some embodiments, the needle assembly 321 can be removably coupled to the medicament container 310 by the coupler 325. The needle assembly 321 and/or the coupler 325 can be any suitable needle assembly and coupler, respectively, of the types shown and described in U.S. patent application Ser. No. 12/173,084, entitled "Apparatus and Methods for Retaining a Needle on a Medical Injector," filed Jul. 15, 2008, which is incorporated herein by reference in its entirety. In some embodiments, for example, the coupler 325 can be, for example, a press-fit Luer fitting (e.g., a Luer-Slip™ fitting), a twist-on Luer fitting (e.g., a Luer-Lok™ fitting) and/or the like.

The actuator assembly 350, which is configured to actuate the medical injector 300 to inject the medicament 318, is coupled to the proximal end portion 311 of the medicament container 310 via the adapter 330. Said another way, the actuator assembly 350 (which includes a pressurized fluid container 351) is coupled to the proximal end portion 311 of the medical container 310 without any substantial intervening hardware (e.g., hoses, tubes or the like). Said yet another way, the actuator assembly 350 and the medicament container 310 form a substantially rigid member that can be held and/or manipulated via a single hand. More particularly, the actuator assembly 350 is coupled to the medicament container 310 such that a longitudinal center line $C_L$ (see e.g., FIG. 7) of the actuator assembly 350 is substantially coaxial with the longitudinal axis $A_L$ of the medicament container 310. In this manner, as described in more detail below, the medical injector 300 has a self-contained source of energy with which the medical injector 300 can be non-manually actuated. Similarly stated, the medical injector 300 is a self-contained, pressurized medical injector.

Figure 8:
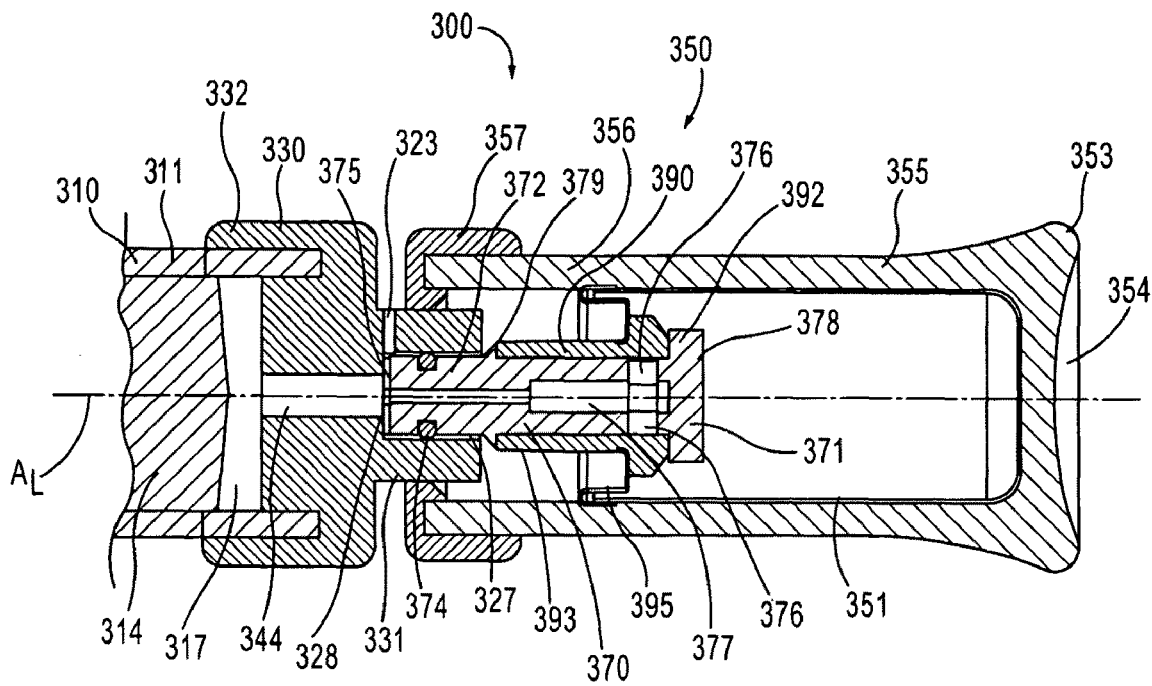
FIGS. 8 and 9 are cross-sectional views of the portion of the medical injector shown in FIG. 5 taken along line X-X, in a first configuration and a second configuration, respectively.
Figure 9:
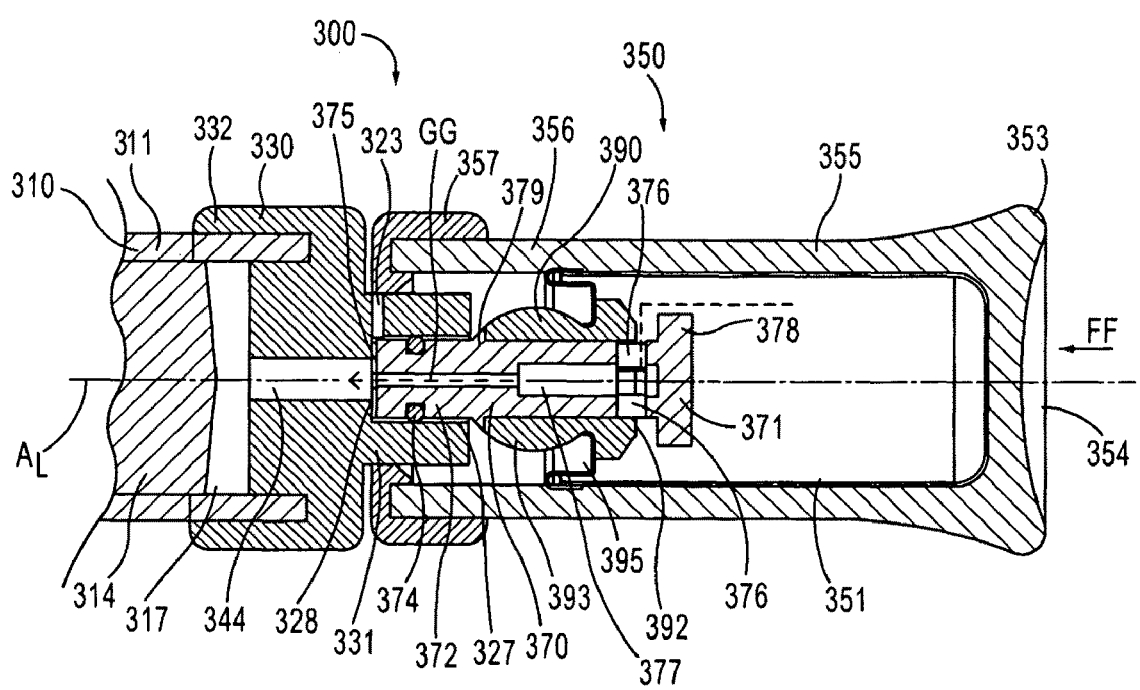

As shown in FIGS. 8 and 9, the adapter 330 includes a proximal end portion 331 and a distal end portion 332. The adapter 330 defines a central lumen 344, a proximal end opening 327 and a vent lumen 323. The distal end portion 331 of the adapter is coupled to the proximal end portion 311 of the medicament container 310 such that the central lumen 344 is in fluid communication with the second internal portion 317 of the medicament container 310. As described in more detail below, a valve stem 370 of the actuator assembly 350 is disposed within the proximal end opening 327 of the adapter 330 to couple the actuator assembly 350 to the adapter 330.

Figure 7:
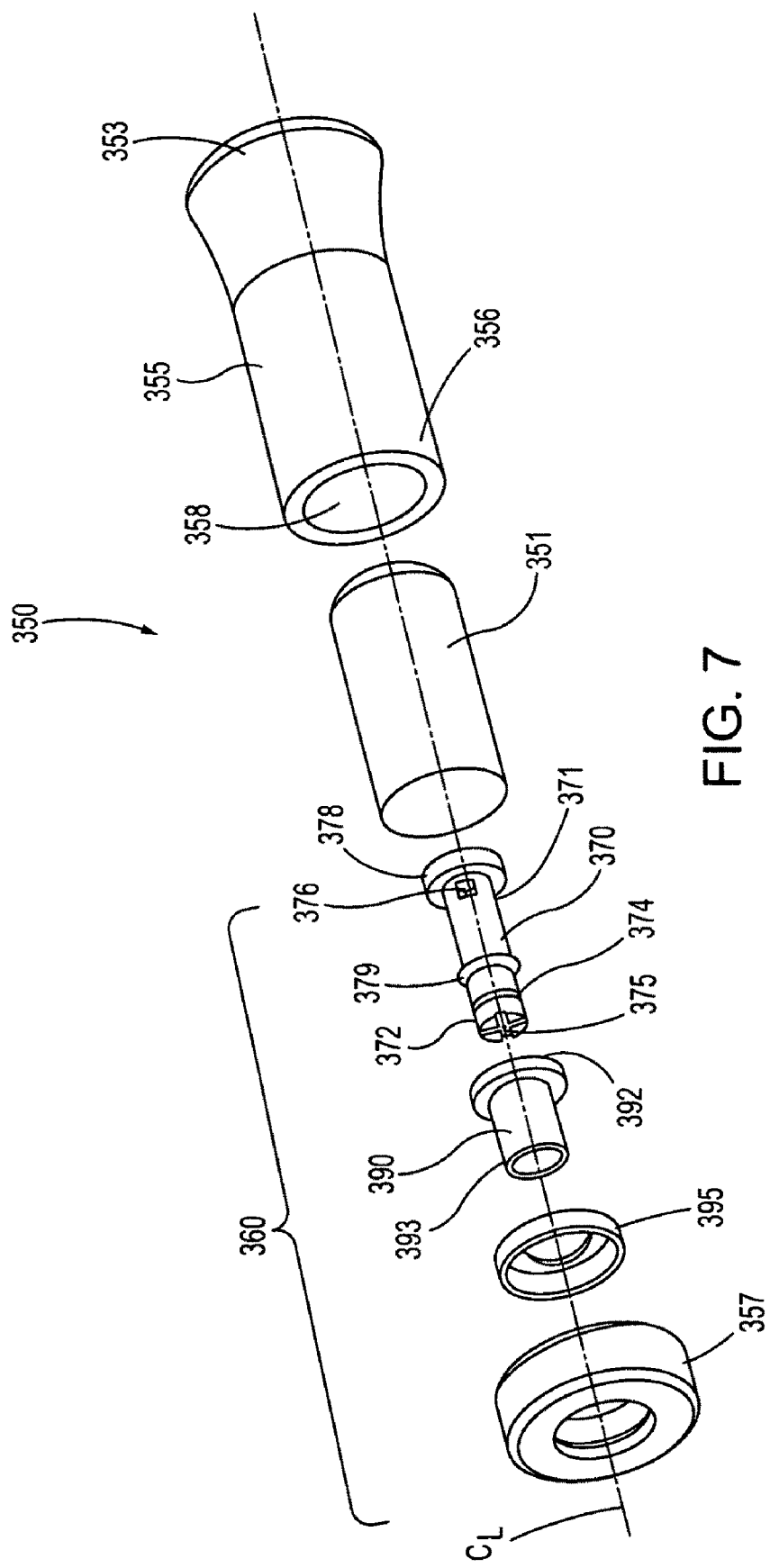

As shown in FIG. 7, the actuator assembly 350 includes a housing 355, a pressurized fluid container 351 and a regulator assembly 360. The housing 355 has a proximal end portion 353, a distal end portion 356 and defines a lumen 358 (see FIG. 7). As shown in FIGS. 8 and 9, the proximal end portion 353 defines a recess 354 configured to receive a user's thumb (not shown).

The pressurized fluid container 351 is disposed within the lumen 358 of the housing 355 at the proximal end portion 353 of the housing 355, and contains a pressurized fluid. The pressurized fluid contained within the pressurized fluid container 351 can be any pressurized fluid (e.g., pressurized gas and/or pressurized liquid) of the types described herein. For example, in some embodiments, the pressurized fluid container 351 can contain a propellant including fluorinated alkanes (e.g., 3,1,1,2-tetrafluoroethane (HFA 334a) and I,1,1,2,3,3,3-heptafluoropropane (HFA 227)). As described in more detail below, the pressurized fluid can be conveyed via the regulator assembly 360 into the second internal portion 317 of the medicament container 310 to move the piston 314 within the medicament container 310. In this manner, the pressurized fluid container 351 provides a source of energy that can non-manually move the piston 314 to cause injection of the medicament.

As shown in FIGS. 8 and 9, the pressurized fluid container 351 and the housing 350 are configured to collectively move relative to the medicament container 310 between a first position and a second position, as shown by the arrow FF in FIG. 9. Similarly stated, the medical injector 300 can be moved between a first configuration (corresponding to the first position of the pressurized fluid container 351) and a second configuration (corresponding to the second position of the pressurized fluid container 351). As described in more detail below, when the medical injector 300 is in the first configuration, the regulator assembly 360 fluidically isolates the pressurized fluid container 351 from the second internal portion 317 of the medicament container 310. When the medical injector 300 is in the second configuration, the regulator assembly 360 fluidically couples the pressurized fluid container 351 and the second internal portion 317 of the medicament container 310.

As shown in FIGS. 7-9, the regulator assembly 360 includes a valve stem 370, a valve seal 390, and a vent seal 357. The valve stem 370 includes a proximal end portion 371 and a distal end portion 372, and defines a lumen 377. The distal end surface of the valve stem 370 defines two vent grooves 375. When the actuator assembly 350 is coupled to the proximal end portion 311 of the medicament container 310, the distal end portion 372 of the valve stem 370 is disposed within the proximal end opening 327 of the adapter 330 such that the distal end surface of the valve stem 370 is in contact with a mounting surface 328 of the adapter 330. As shown in FIG. 8, the vent grooves 375 are arranged to provide a flow path between a central lumen 344 of the adapter 330 and the vent lumen 323 defined by the adapter 330. In this manner, when the medical injector 300 is in the first configuration the second internal portion 317 of the medicament container 310 can be placed in fluid communication with a region outside of the medicament container 310 via the central lumen 344, the vent grooves 375 and the vent lumen 323.

The distal end portion 372 of the valve stem 370 includes a seal 374. The distal end portion 372 of the valve stem 370 is secured within the opening 327 of the adapter 330 by an interference fit between the seal 374 and an inner surface of the adapter 330. Moreover, the seal 374 is configured to engage an inner surface of the adapter 330 to form a substantially fluid-tight seal between the valve stem 370 and inner surface of the adapter. In other embodiments, the distal end portion 372 of the valve stem 370 can be secured within the opening 327 by any suitable mechanism. In some embodiments, for example, the distal end portion 372 of the valve stem 370 can be secured within the opening 327 by an adhesive, a weld joint, an interference fit or the like.

The proximal end portion 371 of the valve stem 370 includes a head 378 and defines openings 376. The openings 376 extend through the side wall of the valve stem 370 and are in fluid communication with the lumen 377 of the valve stem 370. The valve seal 390 is disposed about the proximal end portion 371 of the valve stem 370 such that a distal end portion 393 of the valve seal 390 engages a shoulder 379 of the valve stem 370. More particularly, the valve seal 390 is constructed from an elastomer such that the valve seal 390 can expand to fit over the shoulder 379 during assembly. As shown in FIG. 8, when the medical injector 300 is in the first configuration, a seat surface 392 of the valve seal 390 is in contact with the head 378 of the valve stem 370 to form a substantially fluid-tight seal. In this manner, when the medical injector 300 is in the first configuration, the valve seal 390 and the head 378 fluidically isolate the openings 376 from the pressurized fluid container 351.

As shown in FIGS. 8 and 9, a mounting ring 395 is coupled to an end portion of the pressurized fluid container 351 to form a fluid-tight seal. The mounting ring 395 can be coupled to the pressurized fluid container 351 in any suitable manner, such as, for example, by a weld, and adhesive, an interference fit or the like. The mounting ring 395 is also coupled to the valve seal 390, for example, by an adhesive, a thermal bond or the like. In this manner, a portion of the regulator assembly 360 (i.e., the head 378 of the valve stem 370 and the seat surface 392 of the valve seal 390) are enclosed within the pressurized fluid container 351. Thus, the mounting ring 395, the valve seal 390 and the valve stem 370 can selectively fluidically isolate the pressurized fluid container 351.

The medical injector 300 can be moved from the first configuration (FIG. 8) to the second configuration (FIG. 9) when the protrusions 316 are engaged by the first finger and the second finger (not shown) of the user. When engaged in this manner, the recess 354 of the housing 355 can receive the user's thumb (not shown) such that the medical injector 300 can be grasped in a syringe-style grasp. Thus, the user can move the medical injector 300 from the first configuration to the second configuration by moving the thumb closer to the first finger and the second finger. In this manner, the pressure exerted by the user's thumb on the proximal end portion 353 of the housing 355 causes the housing 350 (and therefore the pressurized fluid container 351) to move relative to the medicament container 310. The housing 350 and the pressurized fluid container 351 can move relative to the medicament container 310 between the first position (e.g., a closed position, as shown in FIG. 8), the second position (e.g., an opened position, as shown in FIG. 9), and any number of positions therebetween, or beyond the second position. In this manner, the regulator assembly 360 can regulate the flow rate of pressurized fluid from the pressurized fluid container 351 to the second internal portion 317 of the medicament container 310, as described below.

When the medical injector 300 is in the first configuration, the seat surface 392 of the valve seal 390 is in contact with the head 378 of the valve stem 370 to form a substantially fluid-tight seal. In this manner, when the medical injector 300 is in the first configuration, the valve seal 390 and the head 378 fluidically isolate the openings 376 from the pressurized fluid container 351. Thus regulator assembly 360 fluidically isolates the pressurized fluid container 351 from the second internal portion 317 of the medicament container 310.

When the housing 350 and the pressurized fluid container 351 are moved relative to the medicament container 310 (as shown by the arrow FF in FIG. 9), the distal end portion 393 of the valve seal 390 is compressed between the shoulder 379 of the valve stem 370 and the mounting ring 395. In this manner, when the housing 350 and the pressurized fluid container 351 are moved relative to the medicament container 310, the distal end portion 393 of the valve seal 390 is deformed. Said another way, a length of the valve seal along the longitudinal axis $A_L$ is decreased. Thus, when the housing 350 and the pressurized fluid container 351 are moved relative to the medicament container 310, the valve seat surface 392 is moved distally away from the head 378 of the valve stem 370. In this manner, pressurized fluid from within the pressurized fluid container 351 can flow through the openings 376 and the lumen 377 of the valve stem 370 and into the second internal portion 317 of the medicament container, as shown by the arrow GG in FIG. 9. Similarly stated, in this manner, the regulator assembly 360 fluidically couples the pressurized fluid container 351 and the second internal portion 317 of the medicament container 310. The pressurized fluid within the second internal portion 317 of the medicament container 310 exerts a force on the piston 314, causing the piston 314 to move within the medicament container 310, as described above.

When the medical injector 300 is in the second configuration, vent seal 357 is disposed about the vent lumen 323. Thus, when the medical injector 300 is in the second configuration, the vent seal 357 obstructs the vent flow path from the second internal portion 317 of the medicament container 310, thereby fluidically isolating the second internal portion 317 from the region outside of the medicament container 310. The vent seal 357 can be constructed from any suitable material for forming a fluid tight seal with the proximal end portion 331 of the adapter 330.

When the medical injector 300 is in the second configuration, the deformation of the distal end portion 393 of the valve seal 390 produces an axial force in the proximal direction on the mounting ring 395. Thus, the valve seal 390 biases the medical injector 300 in the first configuration. The valve seal 390 can be constructed from any suitable material such that a desired force can be produced for a given magnitude of deformation. Said another way, the valve seal 390 can be configured to produce any suitable biasing force when the medical injector is in the second configuration.

When the user removes the force from the proximal end portion 353 of the housing 355 (e.g., by removing the thumb), the biasing force produced by the valve seal 390 causes the housing 350 and the pressurized fluid container 351 to move proximally relative to the medicament container 310 (opposite the arrow FF). In this manner, when the user removes the force from the proximal end portion 353 of the housing 355, the medical injector 300 returns to the first configuration. When the medical injector 300 is in the first configuration, the vent seal 357 is disposed apart from the vent lumen 323. In this manner, the pressurized fluid within the second internal portion 317 of the medicament container 310 can flow out of the second internal portion 317 to a region outside of the medicament container 310 via the central lumen 344, the vent grooves 375 and the vent lumen 323. In this manner, any of the residual pressurized fluid within the medicament container 310 can be vented such that when the medical injector 300 is returned to the first configuration, the force on the piston 314 is removed substantially instantaneously.

As described above, the housing 350 and the pressurized fluid container 351 can move relative to the medicament container 310 between any number of opened positions (i.e., positions in which a portion of the openings 376 are uncovered). In this manner, the regulator assembly 360 can regulate the flow rate of pressurized fluid from the pressurized fluid container 351 to the second internal portion 317 of the medicament container 310. By regulating the flow rate of the pressurized fluid into the second internal portion 317, the distance and velocity with which the piston 314 travels within the medicament container 310 is controlled. Said another way, by regulating the flow rate of the pressurized fluid into the second internal portion 317, the user can control the flow rate and amount of medicament injected during an injection event.

In some embodiments, for example, the flow rate of the medicament can be regulated to maintain a substantially constant flow rate of the medicament through the needle during an injection event. Said another way, when a dermal filler is being injected, the flow rate of the dermal filler can be regulated to produce a substantially uniform bead of medicament within the skin. For example, in some embodiments, the flow rate of the medicament can be regulated to a substantially constant flow rate of at least approximately 0.02 cubic centimeters per minute. In other embodiments, the flow rate of the medicament can be regulated to a substantially constant flow rate of between approximately 0.02 cubic centimeters per minute and 0.5 cubic centimeters per minute. In yet other embodiments, the flow rate of the medicament can be regulated to a substantially constant flow rate of as much as 3 cubic centimeters per minute. In still other embodiments, the flow rate of the medicament can be regulated to a substantially constant flow rate greater than 3 cubic centimeters per minute.

Although the flow rate of the medicament through the distal end portion of the needle is described above as being regulated to a substantially constant value, in some embodiments, the flow rate of the medicament can be selectively varied during the injection process. In this manner, when a the medical injector 300 is used to inject a dermal filler, the user can produce a bead and/or set of beads of medicament within the skin having spatially varied volume.

Figure 10:
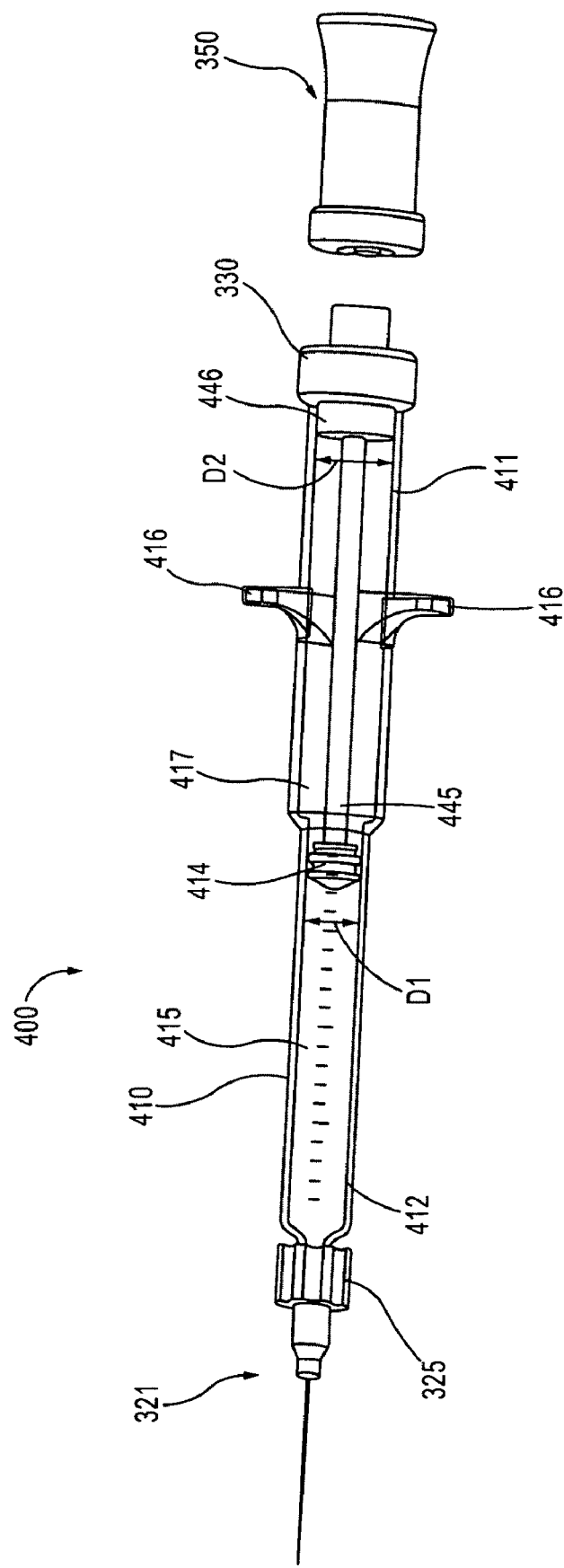
FIG. 10 is a perspective view of a medical injector including a self-contained source of pressurized fluid according to an embodiment.

Although the medicament container 310 is shown as having a substantially constant diameter, in other embodiments, a medicament container can have any suitable size and/or shape. For example, in some embodiments, a first portion of a medicament container can have a first diameter and a second portion of a medicament container can have a second diameter. Such an arrangement can be used, for example, to amplify the pressure of the pressurized fluid as it produces a force on a medicament during an injection event. For example, FIG. 10 shows a medical injector 400 according to an embodiment having a medicament container 410 having different diameters. The medical injector 400 includes a medicament container 410, a needle assembly 321, an actuator assembly 350 and an adapter 330. Because the needle assembly 321, the actuator assembly 350 and the adapter 330 are the same as those described above with reference to the medical injector 300, no further description of these components is provided below.

The medicament container 410 has a proximal end portion 411 and a distal end portion 412. The distal end portion 412 of the medicament container 410 includes a first piston 414 movably disposed therein such that the medicament container 410 is divided by the first piston 414 into a first internal portion 415 and a second internal portion 417. The first piston 414 is disposed within the medicament container 410 such that the first internal portion 415 of the medicament container 410 is fluidically isolated from the second internal portion 417 of the medicament container 410. The first piston 414 has a diameter D1 (i.e., the inner diameter of the distal end portion 412 of the medicament container 410). The first internal portion 415 of the medicament container 410 contains a medicament, such as, for example a dermal filler.

An outer surface of the second portion 411 of the medicament container 410 includes two protrusions 416 extending radially from the medicament container 410. The protrusions 416 are configured to engage at least a first finger (e.g., an index finger) and a second finger (e.g., a middle finger) of a user. In this manner, a user can grasp the medicament container 410 to actuate the medical injector 400 and/or otherwise manipulate the medical injector 400.

The proximal end portion 411 of the medicament container 410 includes a second piston 446 and a push rod 445 movably disposed therein. In this manner, the second piston 446 defines a third internal portion (not shown in FIG. 10). The second piston 446 is disposed within the medicament container 410 such that the second internal portion 417 of the medicament container 410 is fluidically isolated from the third internal portion of the medicament container 410. The second piston 446 has a diameter D2 (i.e., the inner diameter of the proximal end portion 411 of the medicament container 410).

As shown in FIG. 10, the push rod 445 is coupled to the first piston 414 and the second piston 446. In this manner, when the medicament injector 400 is actuated (via the actuation assembly 350), a force acting on the second piston 446 is transferred directly to the first piston 414. In this manner, the force exerted by the pressurized fluid on the second piston 446 is transferred to the first piston 414.

The corresponding pressure of the dermal filler in the first internal portion 415 of the medicament container 410 (P1) and the pressure of the pressurized fluid conveyed into the third internal portion of the medicament container 410 (P2) are defined by equations (1) and (2) below:

$$P1 = F/A1$$

$$P2 = F/A2,$$

where F is the force exerted by the pressurized fluid on the second piston 446, and A1 and A2 are the surface area of the first piston 414 and the second piston 446, respectively. The area A1 is proportional to the diameter D1 squared and the area A2 is proportional to the diameter D2 squared. Because the force F acting on the first piston 414 is the same as the force F acting on the second piston 446 under steady-state conditions, equations (1) and (2) can be rearranged to define the relationship between the pressure P2 of the pressurized fluid and the pressure P1 of the dermal filler:

$$P1 = (A2/A1) * P2.$$

As illustrated by equation (3), the delivery pressure P1 of the dermal filler in the medicament container can be controlled by controlling the pressure P2 of the pressurized fluid in the hand piece 449 and/or by adjusting the area ratio (also referred to as the amplification factor) of the second piston 446 and the first piston 414. In this manner, the medicament container 410 is configured to amplify the pressure of the pressurized fluid.

Although the distal end portion 411 and the proximal end portion 412 of the medicament container 410 are shown as having different sizes (i.e., D1 and D2) and being monolithically constructed, in other embodiments, a medical injector can include a medicament container that is constructed separately from a pressure amplifier. For example, in some embodiments, a medical injector can include a clip-on amplifier of the types shown and described in U.S. patent application Ser. No. 12/114,194, entitled "Apparatus and Methods for Injecting High Viscosity Dermal Fillers," filed May 2, 2008, which is incorporated herein by reference in its entirety.

Figure 11:
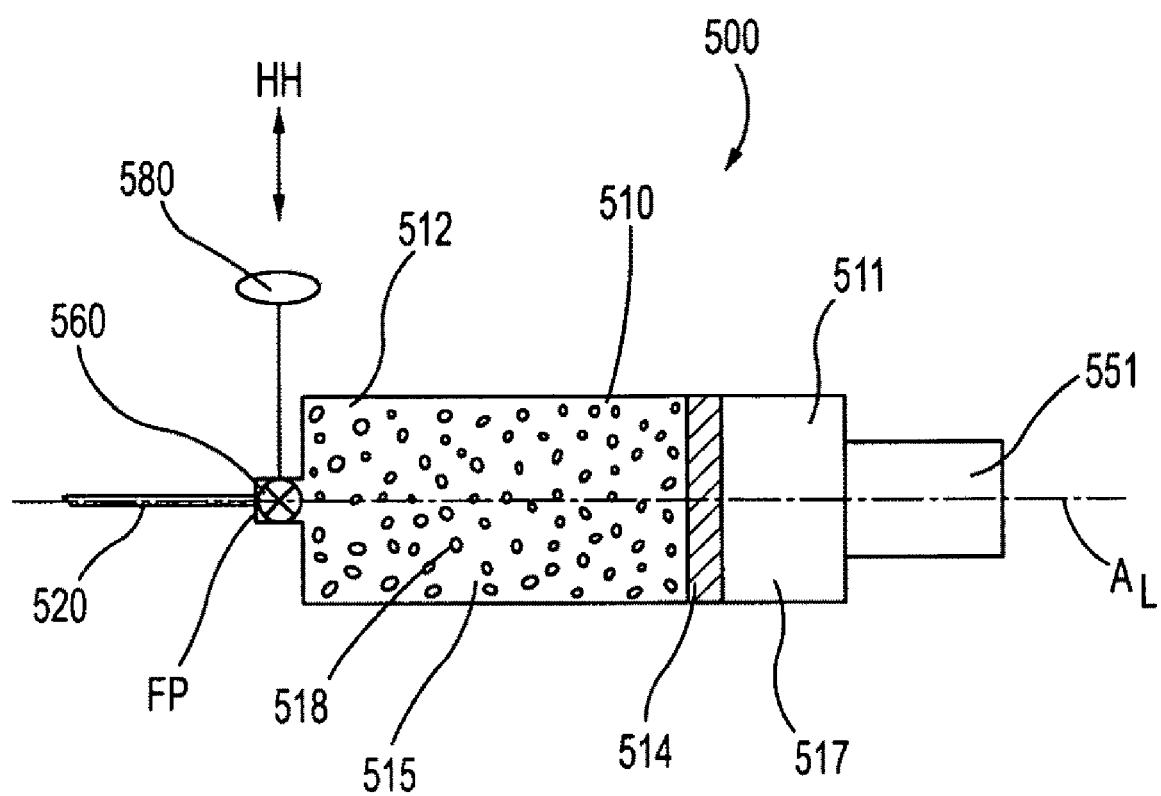
FIG. 11 is schematic illustration of a medical injector according to an embodiment.
Figure 12:
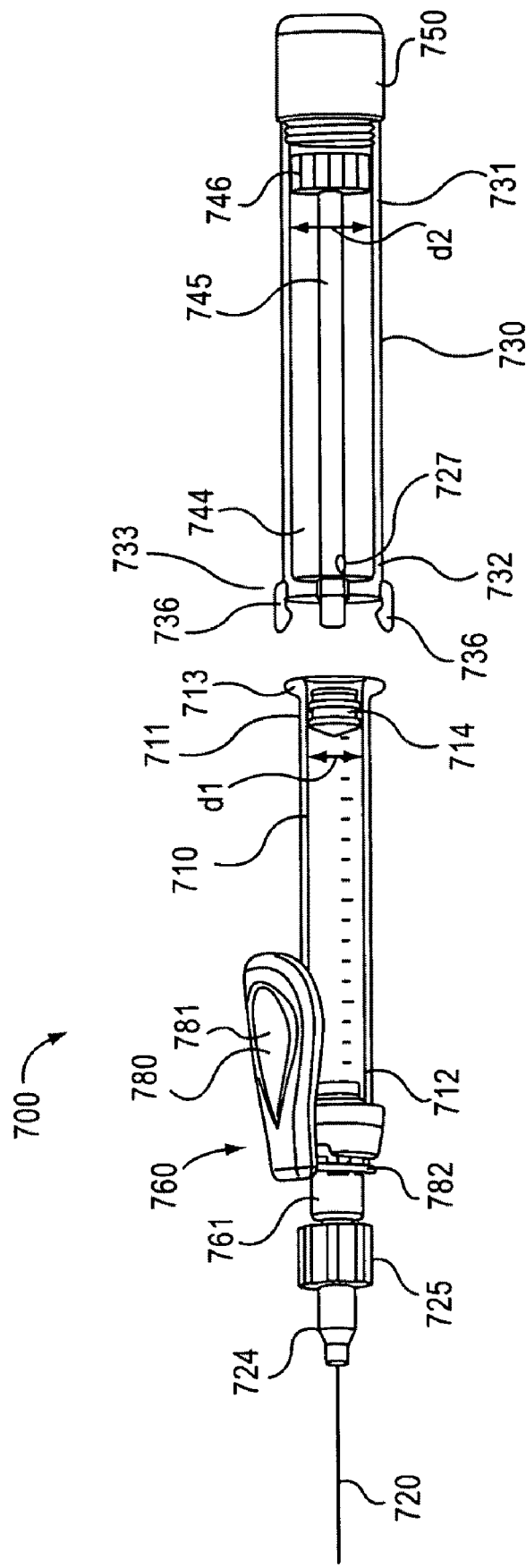
FIG. 12 is a perspective view of a medical injector including a self-contained source of pressurized fluid according to an embodiment.

Although the regulator 360 is shown and described above as controlling flow rate of dermal filler by regulating the flow rate of the pressurized fluid delivered from the source of pressurized fluid 351 to the medicament container 310, in other embodiments, a regulator can regulate the flow rate of dermal filler by obstructing and/or modifying a flow path of the dermal filler. Similarly stated, although the regulator assembly 360 is shown and described above as being disposed outside of the flow path of the dermal filler, in other embodiments, a regulator can have at least a portion disposed within the flow path of the dermal filler. For example, FIG. 11 is a schematic illustration of a medical injector 500 according to an embodiment having a valve mechanism 560 configured to restrict a medicament flow path.

The medical injector 500 includes a medicament container 510, a needle 520 and a valve mechanism 560. The medicament container 510 has a proximal end portion 511 and a distal end portion 512, and defines a longitudinal axis $A_L$. The medicament container includes a piston 514 movably disposed therein such that the medicament container 510 is divided by the piston 514 into a first internal portion 515 and a second internal portion 517. In some embodiments, for example, the piston 514 can be disposed within the medicament container 510 such that the first internal portion 515 of the medicament container 510 is fluidically isolated from the second internal portion 517 of the medicament container 510. The first internal portion 515 of the medicament container 510 is configured to contain a medicament 518 of the types shown and described herein.

The needle 520 is coupled to the distal end portion 512 of the medicament container 510 such that the needle 520 is in fluid communication with the first internal portion 515 of the medicament container 510. Similarly stated, the needle 520 is coupled to the distal end portion 512 of the medicament container 510 such a flow path FP is defined between the first internal portion 515 of the medicament container 510 and the needle 520. The needle 520 can be coupled to the medicament container 510 by any suitable mechanism. For example, in some embodiments, the needle 520 can be coupled to the medicament container 510 by a Luer fitting that provides a substantially fluid-tight seal (i.e., a seal that that substantially prevents a liquid and/or a gas from passing therethrough) between the needle 520 and the medicament container 510.

The pressurized fluid container 551 is coupled to the proximal end portion 511 of the medicament container 510. The pressurized fluid container 551 can be selectively placed in fluid communication with the second internal portion 517 of the medicament container 510. In this manner, a pressurized fluid that can be conveyed into the second internal portion 517 of the medicament container 510 to move the piston 514 within the medicament container 510. Similarly stated, the pressurized fluid container 551 provides a source of energy that can non-manually move the piston 514 to cause injection of the medicament 518. The pressurized fluid contained within the pressurized fluid container 551 can be any pressurized fluid of the types described herein.

The valve mechanism 560 can be any suitable mechanism for controlling the flow of the medicament 518 during an injection event. Similarly stated, the valve mechanism 560 can be any suitable mechanism for controlling the flow of the medicament 518 through the flow path FP. In some embodiments, for example, the valve mechanism 560 can restrict a portion of the flow path FP. In other embodiments, the valve mechanism 560 can divert a portion of the medicament 518 within of the flow path FP to a location other than the needle 520 (e.g., a return flow loop back into the medicament container 510).

The valve mechanism 560 includes an actuator 580 configured to selective actuate the valve assembly 560. As shown by the arrow HH in FIG. 11, the actuator 580 is configured to move in a direction substantially normal to the longitudinal axis $A_L$ of the medicament container 510 to actuate the valve mechanism. In this manner, the force exerted by a user to move the actuator 580 is less likely to cause inadvertent movement of the needle 520 than a force exerted in a direction substantially parallel to the longitudinal axis $A_L$ of the medicament container 510.

Although the regulator assembly 360 is shown and described above as controlling flow rate of dermal filler by regulating the flow rate and/or the pressure of the pressurized fluid delivered from the source of pressurized fluid 351 to the medicament container 310, in other embodiments, a regulator can regulate the flow rate of dermal filler by obstructing and/or modifying a flow path of the dermal filler. Similarly stated, although the regulator 360 is shown and described above as being disposed outside of the flow path of the dermal filler, in other embodiments, a regulator can have at least a portion disposed within the flow path of the dermal filler. For example, FIGS. 12-15 show a medical injector 700 that includes a self-contained source of pressurized gas to inject a dermal filler according to an embodiment.

The medical injector 700 includes a medicament container 710, a needle 720, a source of pressurized fluid 750, and an adapter 730 configured to couple the medicament container 710 to the source of pressurized fluid. The medicament container 710 has a proximal end portion 711 and a distal end portion 712. The medicament container 710 includes a first piston 714 movably disposed therein. The first piston 714 has a diameter d1. The medicament container 710 is configured to contain a dermal filler having a high viscosity. The regulator 760 is disposed at the distal end portion 712 of the medicament container 710. As described in more detail below, a coupler 725 is attached to the regulator and is configured to removably couple the needle 720 to the regulator, and thus to the distal end portion 712 of the medicament container 710. The coupler 725 can be any suitable coupler, as described above. The distal end portion 712 of the medicament container 710 includes a flange 713 that can be coupled to the adapter 730, as described below.

The adapter 730 includes a proximal end portion 731 and a distal end portion 732. The distal end portion 732 of the adapter 730 includes a coupler 733 configured to removably couple the adapter 730 to the medicament container 710. As described above, the coupler 733 includes two coupling members 736 that are disposed approximately equidistance circumferentially about the coupler 733. Said another way, the coupling members 736 are disposed approximately 180 degrees apart. In this manner the coupling members 736 engage the flange 713 of the medicament container 710 at two distinct circumferential locations when the coupler 733 is coupled to the medicament container 710.

Figure 13:
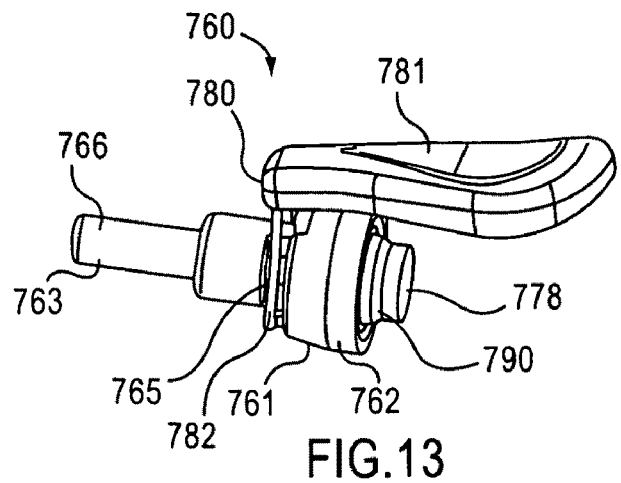
FIG. 13 is a perspective view of a portion of the medical injector shown in FIG. 12.

The adapter 730 defines a lumen 744, within which a second piston 746, having a diameter d2, and a push rod 745 are movably disposed. When the adapter 730 is coupled to the medicament container 710 by the coupler 733, the second piston 746 is coupled to the first piston 714 by the push rod 745. Accordingly, when the adapter 730 is coupled to the medicament container 710 by the coupler 733, a force acting on the second piston 746 is transferred directly to the first piston 714. In this manner, when a pressurized fluid from the source of pressurized fluid 750 is conveyed into the lumen 744, the force exerted by the pressurized fluid on the second piston 746 is transferred to the first piston 714. As shown in FIG. 13, the diameter d2 of the second piston 746 is greater than the diameter d1 of the first piston 714. In this manner, as described above, the pressure within the medicament container 710 can be greater than the pressure supplied by the source of pressurized fluid 750. Said another way, in this manner, the adapter 730 is configured to amplify the pressure of the pressurized fluid from the source of pressurized fluid 750. In some embodiments, for example, diameter d1 of the first piston 714 can be approximately 7 mm (0.28 inches) and the diameter d2 of the second piston 746 can be approximately 12.7 mm (0.5 inches). With such an arrangement, when the pressure provided by the source of pressurized fluid 750 is approximately 534 kPa (76 p.s.i.), the pressure of the dermal filler within the medicament container 710 is approximately 1.7 MPa (250 p.s.i.).

The outer surface of the adapter 730 defines an opening 727 in fluid communication with the lumen 744. The opening 727 is positioned towards a distal end portion 732 of the adapter 730, and is configured to allow fluid within the lumen 744 distally of the second piston 746 to evacuate from the adapter 730 when the second piston 746 moves distally within the adapter 730. In some embodiments, the opening 727 can include a membrane configured to allow fluids to move through the opening in only one direction. In other embodiments, the opening 727 can be configured to allow fluids to flow freely therethrough in any direction.

The source of pressurized fluid 750 is movably coupled to the proximal end portion 731 of the adapter 730. More particularly, the source of pressurized fluid 750 can be actuated by moving the source of pressurized fluid 750 relative to the adapter 730. In this manner, a valve (not shown in FIG. 12) can be opened thereby releasing pressurized fluid from the source of pressurized fluid 750 into the lumen 744 of the adapter 730. In some embodiments, for example, a release valve (not shown in FIG. 12) can be actuated when the source of pressurized fluid 750 is moved relative to the adapter 730, thereby releasing a pressurized fluid into the lumen 744 of the adapter. The source of pressurized fluid 750 can be any suitable source of pressurized fluid, including those described in U.S. Provisional Application Ser. No. 61/016,223, entitled "Self-Contained Pressurized Injection Device," filed Dec. 21, 2007, which is incorporated herein by reference in its entirety.

Figure 14:
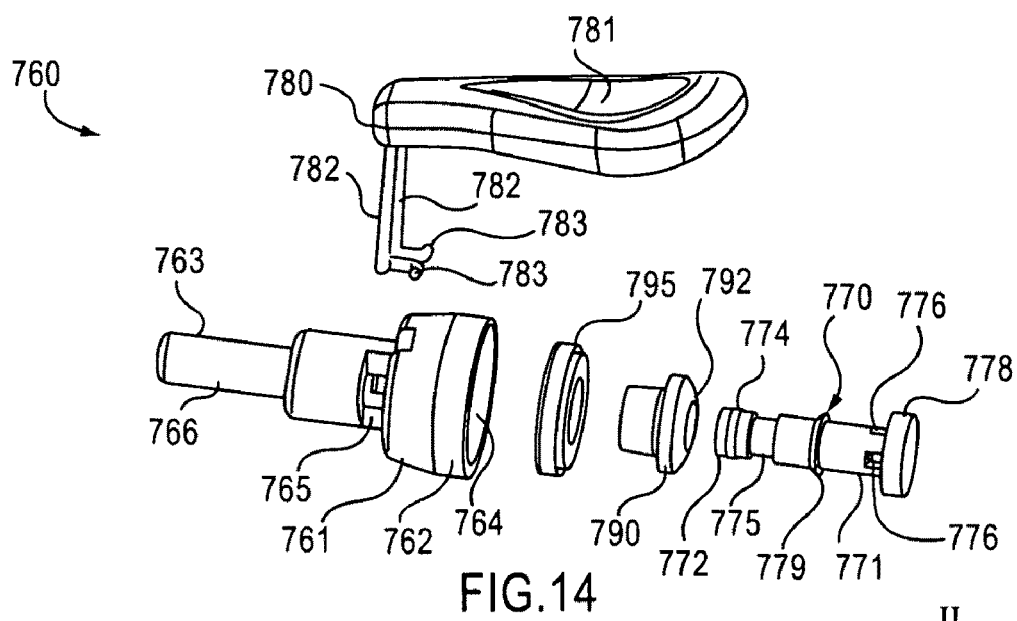
FIG. 14 is an exploded view of the portion of the medical injector shown in FIG. 13.
Figure 15:
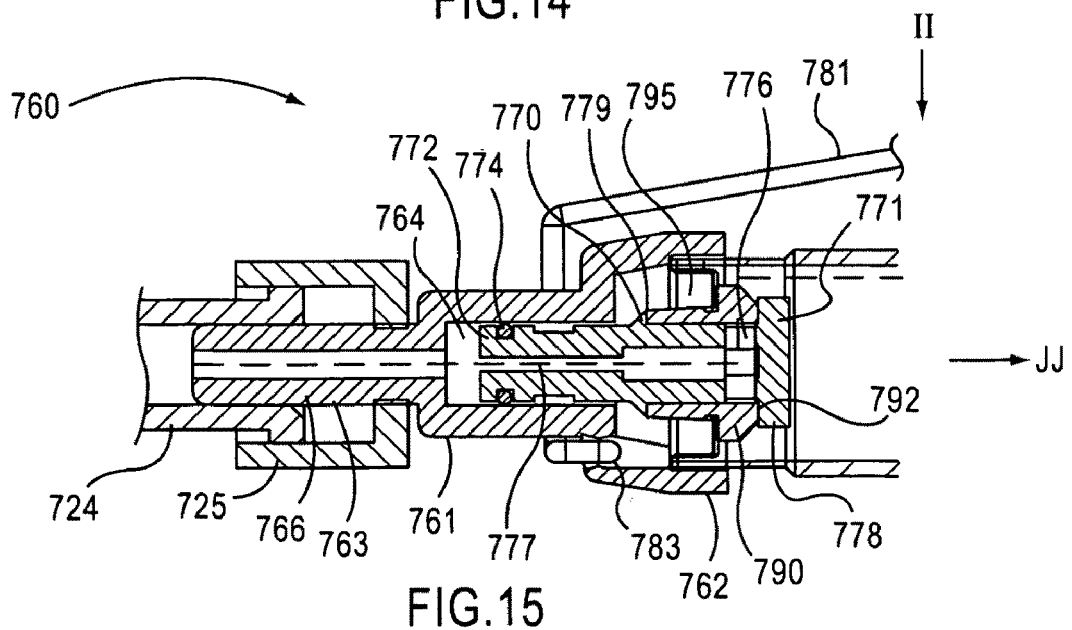
FIG. 15 is a cross-sectional view of a distal portion of the medical injector shown in FIG. 12.

As shown in FIGS. 13-15, the regulator 760 includes a regulator body 761, a valve member 770, a valve actuator 780, and a valve seat 790. The valve actuator 780 includes a lever 781 and two elongated members 782. Each of the elongated members 782 includes a protrusion 783, which can be disposed within the regulator body 761 (see e.g., FIG. 15). In this manner, when lever 781 of the valve actuator 780 is moved, the valve actuator 780 can pivot about the protrusions 783.

The regulator body 761 includes a proximal end portion 762 and a distal end portion 763, and defines a lumen 764 therethrough. The side wall of the regulator body 761 defines openings 765 within which a portion of the actuator 780 can be disposed, as described in more detail herein. The distal end portion 763 of the regulator body 761 includes a stem 766, a portion of which is disposed within the hub 724 of the needle 720. As described above, the coupler 725 is attached to the stem 766, and is configured to removably couple the needle 720 to the regulator 760. The proximal end portion 762 of the regulator body 761 is disposed about and coupled to the distal end portion 712 of the medicament container 710. The proximal end portion 762 of the regulator body 761 can be coupled to the distal end portion 712 of the medicament container 710 by any suitable means, such as, for example, an adhesive, a crimped fit, an external clamp or the like.

As shown in FIG. 15, a mounting ring 795 is disposed between the proximal end portion 762 of the regulator body 761 and the distal end portion 712 of the medicament container 710 to provide a substantially fluid-tight seal between the regulator body 761 and the medicament container 710. Moreover, the valve seat 790 is coupled to the mounting ring 795 such that a seat surface 792 is disposed within the medicament container 710 facing in a proximal direction. In this manner, the mounting ring 795 can position the valve seat 790 relative to the regulator body 761 and/or the valve member 770.

The valve member 770 includes a proximal end portion 771 and a distal end portion 772, and defines a lumen 777. The distal end portion 772 of the valve member 770 includes a shoulder 779, a seal 774, and defines an actuation groove 775. As shown in FIG. 15, the seal 774 is configured to engage an inner surface of the regulator body 761 to form a substantially fluid-tight seal between the valve member 770 and the regulator body 761. The actuation groove 775 is configured to receive a portion of each elongated member 782 of the valve actuator 780. In this manner, as described in more detail herein, movement of the actuator 780 can cause the valve member 770 to move longitudinally within the regulator body 761. The proximal end portion 771 of the valve member 770 includes a head 778 and defines openings 776. The openings 776 extend through the side wall of the valve member 770 and are in fluid communication with the lumen 777 of the valve member 770.

The valve member 770 is movably disposed within the lumen 764 of the valve body 761 between a first position (e.g., a closed position, as shown in FIG. 15), a second position (e.g., a fully opened position, not shown in FIGS. 12-15), and any number of positions therebetween. In this manner, the regulator 760 can regulate the flow rate of dermal filler from the medicament container 710 through the needle 720. When the valve member 770 is in the first position, the head 778 of the valve member 770 is disposed against the seat surface 792 of the valve seat 790 to form a substantially fluid-tight seal, as shown in FIG. 15. Accordingly, when the valve member 770 is in the first position, the dermal filler cannot flow from the medicament container 710 through the needle 720. Said another way, when the valve member 770 is in the first position, the flow rate of the dermal filler from the medicament container 710 is substantially zero. Moreover, because the pressure within the medicament container 710 produces a force on the head 778 in a distal direction, the pressure within the medicament container tends to maintain the valve member 770 in the first position. Additionally, as shown in FIG. 15, when the valve member 770 is in the first position, the shoulder 779 of the valve member 770 is disposed against a distal portion of the valve seat 790. In this manner, the valve member 770 is maintained in the first position by the force of the valve seat 790 on the shoulder 779.

To move the valve member 770 from the first position to the second position, the user can move the lever 781 of the valve actuator 780 inward, as shown by the arrow II in FIG. 15. As described above, the inward movement of the lever 781 causes the valve actuator 780 to pivot about the protrusions 783. In this manner, the elongated members 782 of the valve actuator 780 move proximally. A portion of each of the elongate members 782 is disposed within the actuation groove 775 of the valve member 770. Accordingly, proximal movement of the elongated members 782 causes the valve member 770 to move proximally, as shown by the arrow JJ in FIG. 15. The proximal movement of the valve member 770 causes the head 778 to be spaced apart from the seat surface 792, thereby allowing flow of the dermal filler through the openings 776 and into the lumen 777 of the valve member 770. Said another way, the proximal movement of the valve member 770 causes the head 778 to be spaced apart from the seat surface 792, thereby defining a medicament flow path (as shown by the dashed line in FIG. 15).

Moreover, when the valve member 770 is moved proximally, the shoulder 779 exerts a force on the distal portion of the valve seat 790, thereby causing the distal portion of the valve seat 790 to deform. In this manner, the distal portion valve seat 790 acts as a biasing member to urge the valve member 770 towards the first position.

Although the medical injector 700 is shown and described as include a valve member 770 configured to move within a flow pathway of the medicament, in other embodiments a regulator can include any suitable mechanism for regulating the flow rate of a medicament from a medical injector. For example, in some embodiments, a medical injector can include a regulator devoid a valve member that is movable within the flow pathway. Such an arrangement can, for example, limit inaccuracies in controlling the flow rate of a medicament associated interaction between the valve member and the medicament (e.g., sticking of the valve member).

Figure 16:
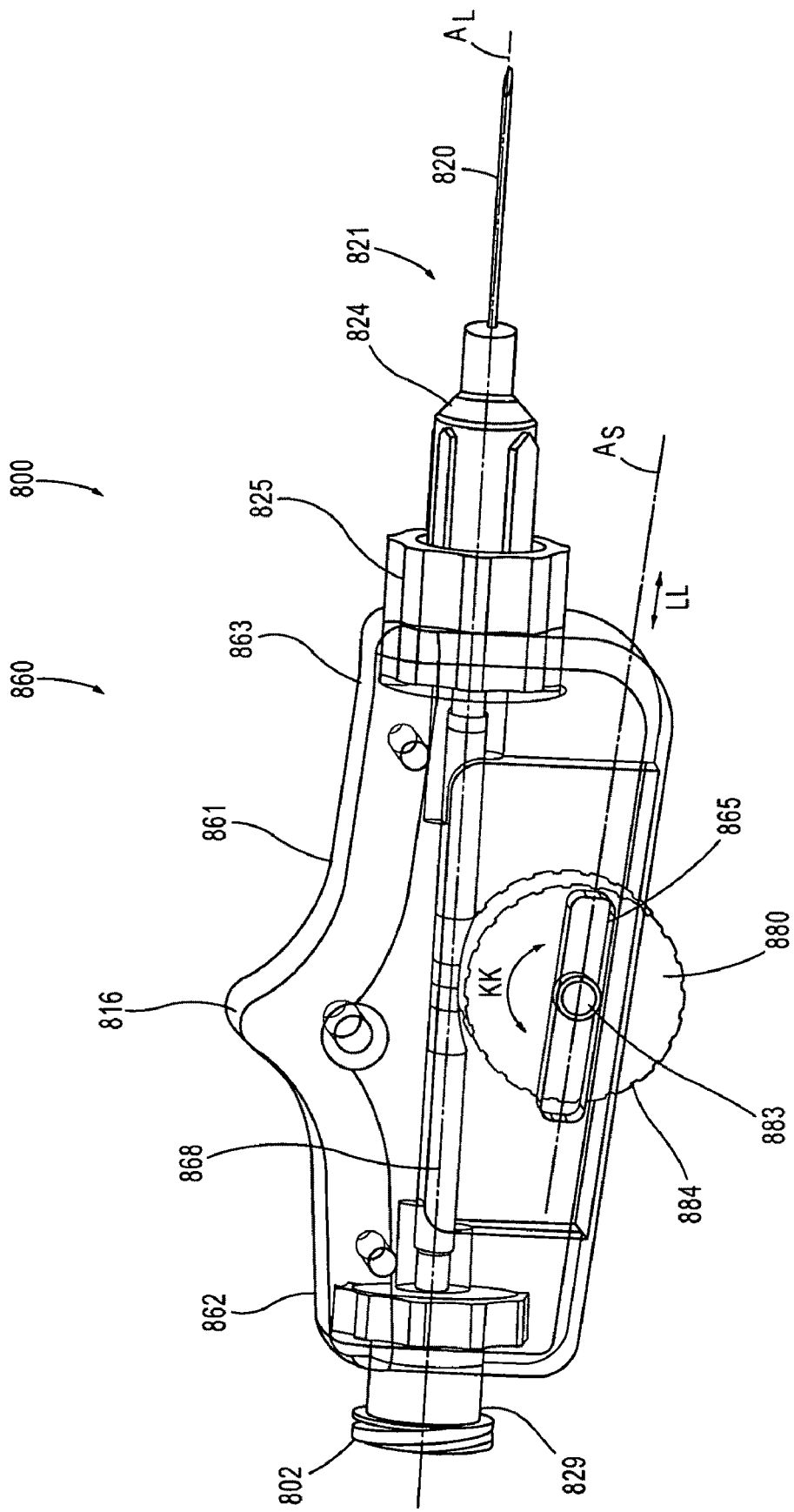
FIG. 16 is a perspective view of a portion of a medical injector according to an embodiment.

For example, FIG. 16 shows a portion of a medical injector 800 according to an embodiment. The medical injector 800 includes a needle assembly 821 and a regulator assembly 860. The needle assembly 821 includes a needle 820 and a needle hub 824 of the types shown and described herein. The regulator assembly 860 is configured to be coupled to a medicament container (not shown) of the types shown and described herein. In this manner, a medicament can be conveyed from the medicament container to the needle assembly 821 via the regulator assembly 860.

The regulator assembly 860 includes a housing 861, a flow tube 868 and an actuator 880. The housing 861 includes a proximal end portion 862 and a distal end portion 863. The distal end portion 863 of the housing 861 includes a coupler 825 configured to couple the needle assembly 821 to the housing 861 such that the needle 820 is in fluid communication with the flow tube 868. In some embodiments, the coupler 825 is a Luer fitting that provides a substantially fluid-tight seal (i.e., a seal that that substantially prevents a liquid and/or a gas from passing therethrough) between the needle 820 and the flow tube 868.

The proximal end portion 862 of the housing 861 includes a coupler 829 configured to couple a medicament container to the housing 861 such that the medicament container is in fluid communication with the flow tube 868. The coupler 829 can be configured to receive a tapered protrusion of a medicament container to form a substantially fluid-tight seal when coupled to the medicament container. The coupler 829 includes a flange 802 that can be received, for example, in a corresponding coupler on the medicament container.

An outer surface of the housing 861 includes a finger grip 816 configured to engage at least a first finger (e.g., an index finger) and a second finger (e.g., a middle finger). In this manner, a user can grasp the housing 861 to insert the needle 820 into the skin of a patient, to actuate the medical injector 800 and/or otherwise manipulate the medical injector 800. The housing 861 defines an internal region within which the flow tube 868 is disposed. More particularly, the flow tube 868 is disposed within housing 861 substantially coaxial with a longitudinal axis $A_L$ of the needle assembly 821 and/or the medicament container (not shown). The housing 861 further defines two slots 865 (only one is shown in FIG. 16) configured to retain the actuator 880, as described in more detail below. The slots define a longitudinal axis $A_S$ that is angularly offset (i.e., non-parallel to) the longitudinal axis $A_L$. In some embodiments, for example, the longitudinal axis $A_S$ can be offset from the longitudinal axis $A_L$ by approximately two to ten degrees.

The actuator 880 has a substantially circular-shaped outer surface 884 and includes a two protrusions 883 (only one shown in FIG. 16). Similarly stated, the actuator 880 is a disc-shaped member. The outer surface 884 includes a series of ridges and/or protrusions that can, for example, assist a user in manipulating the actuator 880. At least a portion of the actuator 880 is disposed within the internal region of the housing 861 such that a portion of the outer surface 884 is in contact with the flow tube 868. More particularly, the actuator 880 is disposed within the internal region of the housing 861 such that the outer surface 884 deforms a portion of the flow tube 868. By changing the amount of deformation, as described below, the flow pathway can be selectively restricted to control the flow of medicament from the medicament injector.

The actuator 880 is movably coupled to the housing 861 such that the protrusions 883 are disposed within the slots 865. In this manner, the actuator 880 can be rotated relative to the housing 861 about the protrusions 883, as shown by the arrow KK in FIG. 16. When the actuator 880 is rotated relative to the housing 861, the actuator 880 also translates relative to the housing 861, as shown by the arrow LL in FIG. 16. Because the direction of linear motion is angularly offset from the longitudinal axis $A_L$, when the actuator 880 translates relative to the housing 861, the actuator 880 is moved closer to or further away from the flow tube 868. In this manner, by rotating the actuator 880 relative to the housing 861, the amount of deformation of the flow tube 868 can be selectively controlled.

In use, the user can grasp the medical injector 800 by engaging the finger grip 816 with a first finger and a second finger (not shown). The user can then place a thumb (not shown) on the outer surface 884 of the actuator 880. Because the position of the actuator 880 relative to the flow tube 868 is based on the location of the actuator 880 within the slots 865, the user can apply an inward force with the thumb without inadvertently adjusting the flow rate of the medicament from the medicament container. Similarly stated, this arrangement allows the user to grasp the medical injector 800 by applying a force to the actuator 800 in a direction substantially normal to the longitudinal axis $A_L$ without adjusting the flow rate of the medicament conveyed from the medical injector 800.

FIGS. 17-20 show a portion of a medical injector 900 according to an embodiment. The medical injector 900 includes a medicament container 910 and a regulator assembly 960. The medicament container 910 has a proximal end portion 911 and a distal end portion 912, and defines a longitudinal axis $A_L$. The medicament container 910 can contain a medicament suitable for being injected into a body, such as, for example a dermal filler, a sub-dermal filler, a therapeutic substance for mesotherapy or the like. Similar to the medicament containers described above, the medicament container can include a piston (not shown) movably disposed therein to transfer a force and/or a pressure from an energy source (not shown) to the medicament to convey the medicament from the medicament container 910 through the regulator assembly 960. The energy source can be any suitable energy source, such as for example, any of the pressurized fluid containers shown and described herein.

Figure 17:
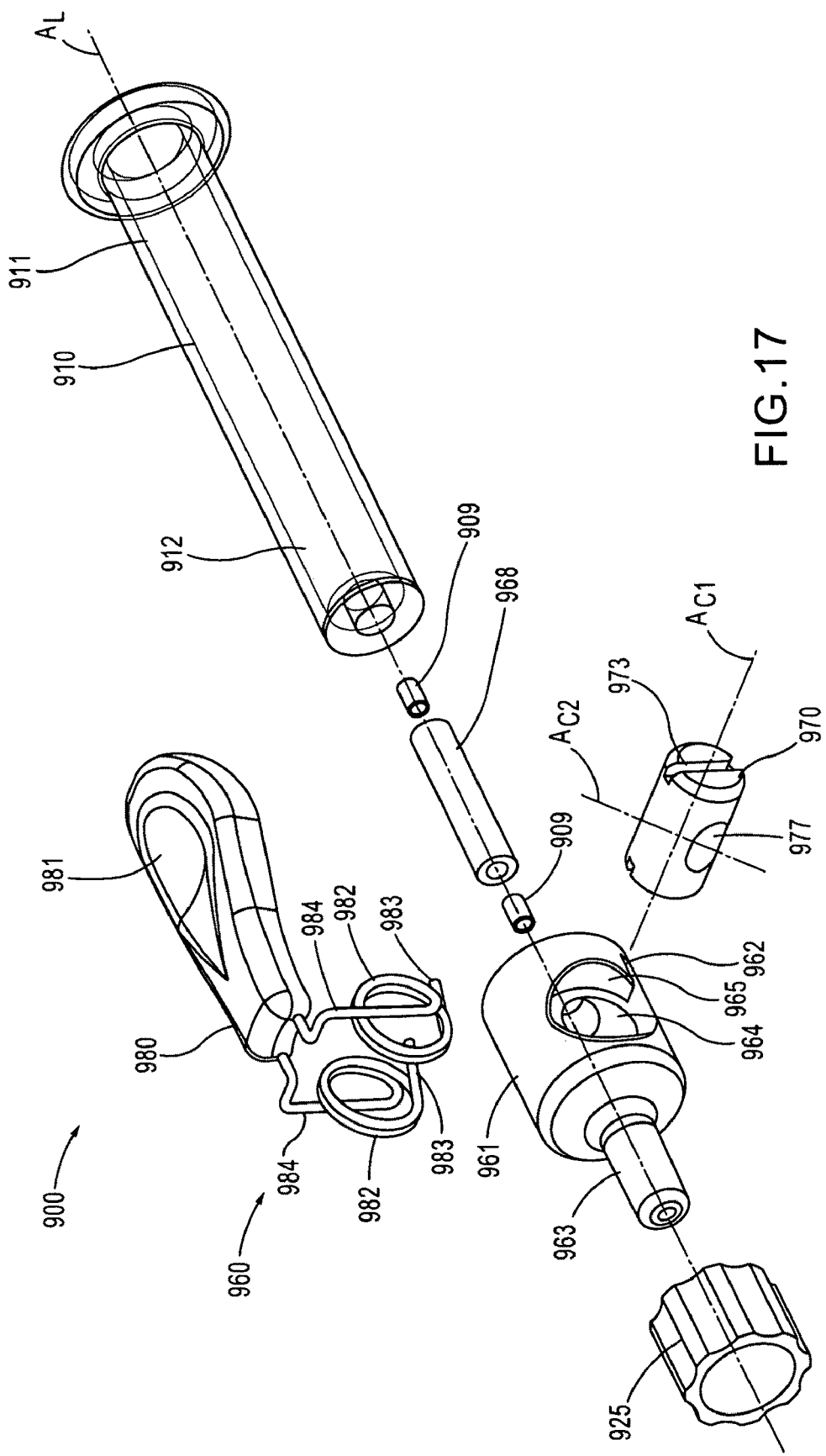
FIG. 17 is an exploded view of a portion of a medical injector according to an embodiment.

The regulator assembly 960 includes a housing 961, a flow tube 968, a pinch cylinder 970, and an actuator 980. The housing 961 includes a proximal end portion 962 and a distal end portion 963. The distal end portion 963 of the housing 961 includes a coupler 925 configured to couple the regulator assembly to a needle assembly (not shown) such that the needle assembly is in fluid communication with the flow tube 968. In some embodiments, the coupler 925 is a Luer fitting that provides a substantially fluid-tight seal (i.e., a seal that that substantially prevents a liquid and/or a gas from passing therethrough) between the needle assembly and the flow tube 968. As shown in FIG. 17, a distal end portion of the flow tube 968 includes a ferrule 909 to reinforce and/or enhance the coupling and/or flow pathway between the flow tube 968 and the needle assembly.

The proximal end portion 962 of the housing 961 is coupled to the distal end portion 912 of the medicament container 910 such that the medicament container 910 is in fluid communication with the flow tube 968. In this manner, the flow tube 968 defines a medicament flow pathway between the medicament container 910 and the needle assembly. The proximal end portion 962 of the housing 961 can be coupled to the distal end portion 912 of the medicament container 910 in any suitable manner. In some embodiments, for example, the distal end portion 912 of the medicament container can be disposed within the proximal end portion 962 of the housing 961 to form an interference fit. In other embodiments, the proximal end portion 962 of the housing 961 can include a coupler (e.g., a Luer fitting) to couple the proximal end portion 962 of the housing 961 to the distal end portion 912 of the medicament container 910. In yet other embodiments, the proximal end portion 962 of the housing 961 can coupled to the distal end portion 912 of the medicament container 910 via a weld, an adhesive bond or the like. As shown in FIG. 17, a proximal end portion of the flow tube 968 includes a ferrule 909 to reinforce and/or enhance the coupling and/or flow pathway between the flow tube 968 and the medicament container 910.

Figure 20:
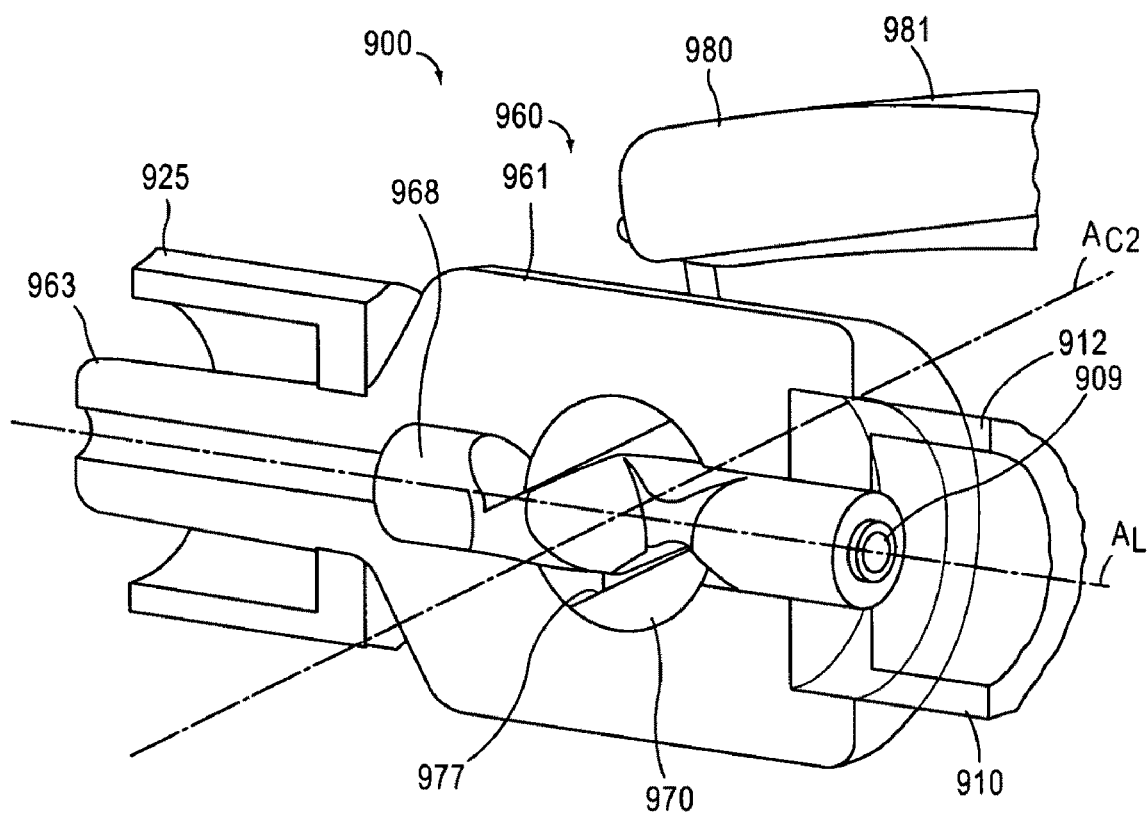
FIG. 20 is a perspective cross-sectional view of the portion of a medical injector shown in FIG. 17 in the first configuration.

The pinch cylinder 970 defines a first axis $A_{C1}$ and a lumen 977 therethrough. The lumen 977 defines a center line $A_{C2}$ that is substantially normal to the first axis $A_{C1}$. Each end of the pinch cylinder 970 defines a retention groove 973. As shown in FIG. 20, the pinch cylinder 970 is disposed within a lumen 964 defined by the housing 961 such that a central portion of the flow tube 968 is disposed within the lumen 977 of the pinch cylinder 970. As described in more detail below, the pinch cylinder 970 can be rotated within the housing 961 to selectively deform, compress and/or "pinch" the central portion of the flow tube 968.

Figure 18:
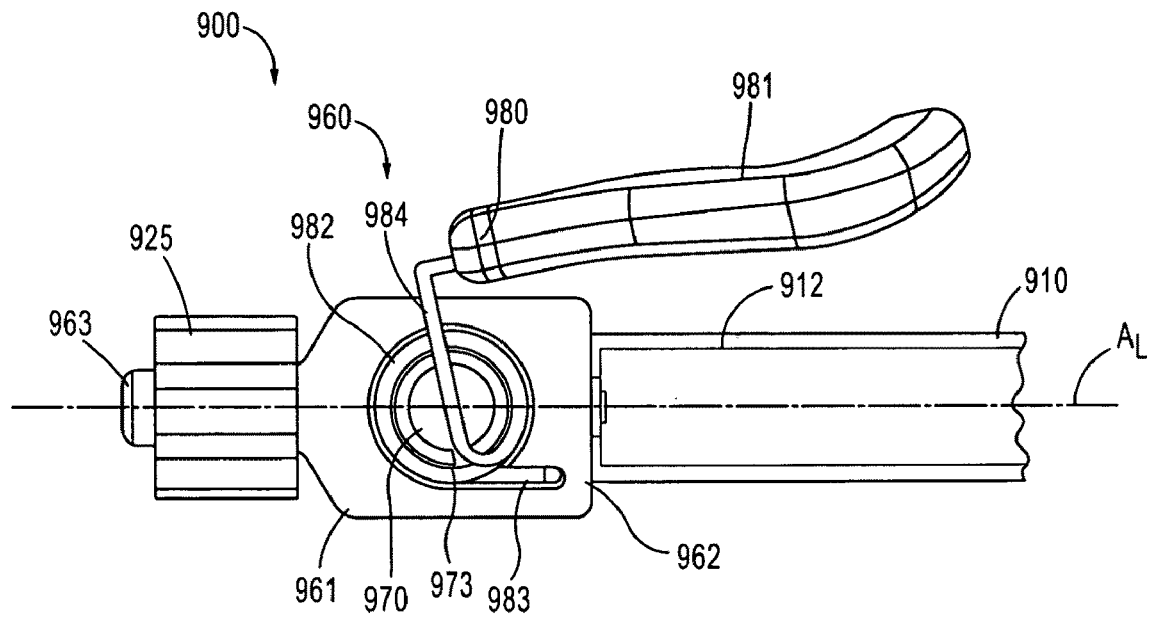
FIGS. 18 and 19 are side views of the portion of a medical injector shown in FIG. 17 in a first configuration and a second configuration, respectively.
Figure 19:
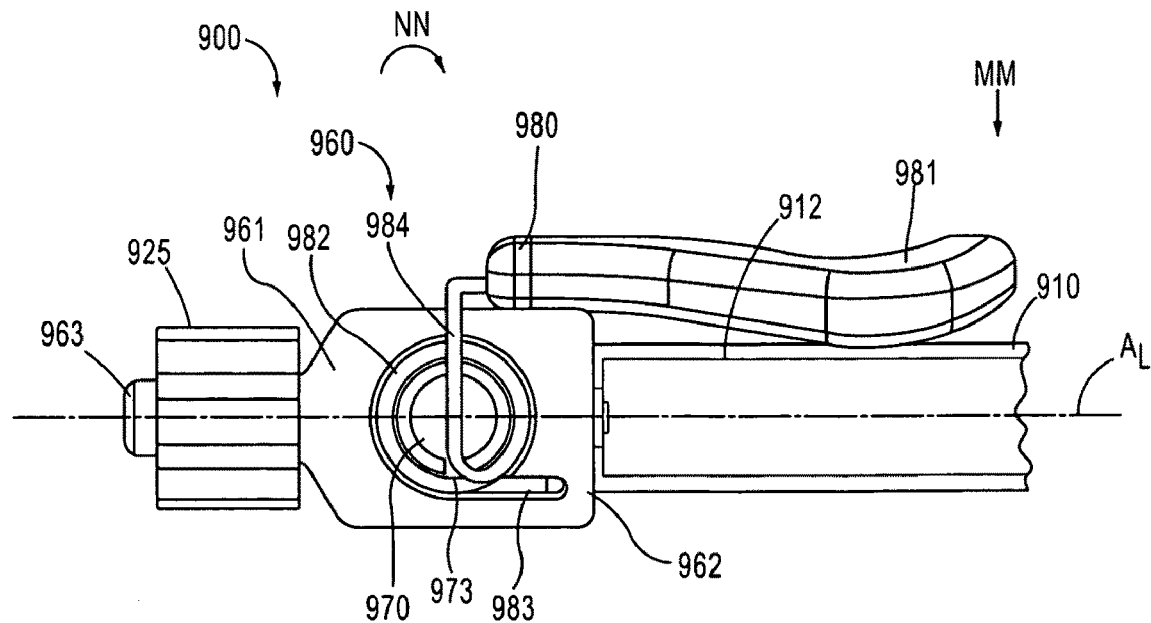

The actuator 980 includes a lever 981 and two coil springs 982. Each of the coil springs 982 includes a retention portion 983. Each coil spring 982 is coupled to the lever 981 by an elongate members 984. The elongate member 984 can be a wire that is monolithically formed with the coil spring 982. A portion of each coil spring 982 is disposed within a corresponding spring pocket 965 (see e.g., FIG. 17) defined the housing 961. As shown in FIGS. 18 and 19, the retention portion 983 of the coil spring 982 is disposed within a mating portion of the spring pocket 965. In this manner, when the coil springs 982 are coupled to the housing 961, rotation of the coil springs 982 relative to the housing 961 is limited.

When the coil springs 982 are coupled to the housing 961, a portion of each elongate member 984 is disposed within the corresponding retention groove 973 of the pinch cylinder 970. In this manner, rotation of the elongate member 984 of each coil spring 982 results in rotation of the pinch cylinder 970 about the first axis $A_{C1}$. Additionally, the coil springs 982 bias the pinch cylinder 970 in a predetermined rotation position within the housing 961. More particularly, as shown in FIGS. 18 and 20, the coil springs 982 bias the pinch cylinder 970 within the housing 961 in a first position, in which the center line $A_{C2}$ of the lumen 977 is angularly offset (i.e., non-parallel to) from the longitudinal axis $A_L$. In some embodiments, for example, the center line $A_{C2}$ can be offset from the longitudinal axis $A_L$ by approximately ten to twenty degrees. In other embodiments, for example, the center line $A_{C2}$ can be offset from the longitudinal axis $A_L$ by up to forty-five degrees.

When the pinch cylinder 970 is in the first position, the medical injector 900 is in the first (or fully closed) configuration. As shown in FIG. 20, when the medical injector 900 is in the first configuration, the pinch cylinder 970 deforms, compresses and/or pinches the central portion of the flow tube 968 such that the medicament cannot flow therethrough. In this manner, the regulator assembly 960 restricts the flow pathway between the medicament container 910 and the needle assembly.

The medical injector 900 can be moved to a second (or fully opened) configuration, or any number of configurations therebetween, by moving the lever 981, as shown by the arrow MM in FIG. 19. Similarly stated, a user can control the flow of the medicament through the flow tube 968 by moving the lever 981 in a direction substantially normal to the longitudinal axis $A_L$. When the lever 981 is moved as shown by the arrow MM, the pinch cylinder 970 rotates within the housing 961 as shown by the arrow NN. When the medical injector 900 is in the fully opened configuration, the center line $A_{C2}$ is substantially parallel to the longitudinal axis $A_L$, and the pinch cylinder 970 does not deform, compress and/or pinch the central portion of the flow tube 968.

The needles shown and described herein can have any suitable bore size and length. For example, in some embodiments, the needle can have a small bore to reduce patient discomfort during a procedure. For example, in some embodiments, any of the needles shown and described herein can define a lumen having a nominal inner diameter of less than or equal to approximately 0.191 millimeters (i.e., a 17 gauge needle). In other embodiments, any of the needles shown and described herein can define a lumen having a nominal inner diameter of less than or equal to approximately 0.140 millimeters (i.e., a 30 gauge needle). In some embodiments, for example, a needle can define a lumen having a nominal inner diameter of approximately 0.114 millimeters (i.e., a 31 gauge needle).

The medicaments and/or dermal fillers described above can be any material suitable for augmenting soft tissue. For example, in some embodiments, any of the medicaments described herein can be a high viscosity dermal filler (i.e., a dermal filler having a viscosity of at least 100 Poise). In other embodiments, any of the medicaments described herein can have a viscosity of at least 1000 Poise (100 N-sec/m$^2$). In yet other embodiments, any of the medicaments described herein can have a viscosity of at least 10,000 Poise. In still other embodiments, any of the medicaments described herein can have a viscosity of at least 100,000 Poise.

In some embodiments, any of the medicaments described herein can be a fluid that is characterized by a substantially linear shear stress as a function of the rate of shear strain applied thereto. Said another way, in some embodiments, any of the medicaments described herein can be a Newtonian fluid having a viscosity that varies substantially only as a function of its temperature and pressure. In other embodiments, any of the medicaments described herein can be a fluid that is characterized by a non-linear shear stress as a function of the rate of shear strain applied thereto. Said another way, in some embodiments, any of the medicaments described herein can be a non-Newtonian fluid having a viscosity that varies according other factors, such as, for example, the magnitude of and/or rate of increase of a force applied to the medicament.

In some embodiments, a medicament and/or dermal filler can include a pain reliever, such as, for example, lidocaine. In other embodiments, a medicament and/or dermal filler can include a colorant and/or a marker. For example, in some embodiments a medicament and/or dermal filler can include a radio-opaque marker. In other embodiments, a medicament and/or dermal filler can include a tattoo ink.

In some embodiments, a dermal filler can include, for example, a side chain crystalline (SCC) polymer of the type disclosed in International Patent Application No. PCT/US2007/023226, entitled "Compositions, Devices and Methods for Modifying Soft Tissue," which is incorporated herein by reference in its entirety. In other embodiments, a dermal filler can include hyaluronic acid. In yet other embodiments, a dermal filler can include polyacrylamide, collagen (either human and/or bovine), polymethylmethacrylate, silicone, calcium hydroxylapatite (CaHA), hydrophilic polyacrylamid gel (PAAG), and/or poly-L-lactic acid hydrogel (PLLA).

In some embodiments, a dermal filler can include any of the following commercially-available dermal fillers: Puragen™ and its derivatives, produced by Mentor Corporation, Belotero® and its derivatives, produced by Merz Pharmaceuticals, BIO-ALCAMID™ and its derivatives, produced by Polymekon S.R.L., Outline® and its derivatives, produced by ProCytech, HylaNew® and its derivatives, produced by Prollenium Medical Technologies, Inc., Restylane® and its derivatives, produced by Q-Med or Medicis Pharmaceutical Corporation, Reviderm USA and its derivatives, produced by Rofil Medical International N.V., Teosyal® and its derivatives, produced by Teoxane Laboratories, Fascian® and its derivatives, produced by Fascia Biosystems, LLC, FG-5017 and its derivatives, produced by Fibrogen, Inc., Amazingel and its derivatives, produced by FuHua High Molecular Matter Company, Ltd., Laresse® Dermal Filler and its derivatives, produced by FzioMed, Inc., Zyderm® and its derivatives, produced by Inamed Corporation, Isolagen® and its derivatives, produced by Isolagen, Inc., MacDermol® and its derivatives, produced by Laboratories ORGéV, Juvé- derm™ and its derivatives, produced by L.E.A. Derm, Hyaluderm® and its derivatives, produced by LCA Pharmaceutical, Silikon® 1000 and its derivatives, produced by Alcon, Inc., Esthèlis and its derivatives, produced by Antesis® S.A., Artefill® and its derivatives, produced by Artes Medical, Inc., Radiesse® and its derivatives, produced by BioForm Medical, Inc., Matridex® and its derivatives, produced by BioPolymer GmbH & Co. KG, Evolence® and its derivatives, produced by ColBar LifeScience Ltd., Aquamid® and its derivatives, produced by Contura International A/S, SurgiDerm® and its derivatives, produced by Labortoire Corneal® Development, Rhegecoll and its derivatives, produced by Dermabiol Institute of Kuhra Vital GmbH, DermaLive® and its derivatives, produced by Derma Tech, and/or Sculptra™ and its derivatives, produced by Dermik® Laboratories.

The pressurized fluid containers described herein can contain any fluid suitable for use as an energy source that can act upon the piston to produce a non-manual injection event. Such fluids can include, for example, a pressurized gas, a vapor pressure based propellant, one or more substances configured to produce a pressurized fluid via a chemical reaction or the like. For example, in some embodiments, any of the pressurized fluid containers described herein can contain carbon dioxide, nitrogen and/or the like at a pressure greater than atmospheric pressure.

In other embodiments, any of the pressurized fluid containers described herein can contain propellant formulated such that the pressure produced by the propellant upon release from the pressurized fluid container does not decrease substantially a function of the amount of propellant remaining in the pressurized fluid container. For example, in some embodiments, a propellant can include a propellant-type alkane, such as, for example, propane, pentane, butane and/or isobutene. A propellant can also include the chlorofluorocarbons (CFCs), such as, for example, trichlorofluoromethane (F11), dichlorodifluoromethane (F12) and/or 1,2-dichloro-1,1,2,2-tetrafluoroethane (F114). A propellant can also include perfluorocarbons (PFC's), such as, for example, perfluorobutane and perfluoropentane; hexafluoro-1,3-butadiene; 1,1,1,2,3,3-hexafluoropropane; and octafluoro-2-butene. In other embodiments, a propellant can include any suitable CFC substitute, such as, for example, hydrofluoroalkanes (HFAs). In some embodiments, for example, a propellant can include 1,1,1,2-tetrafluoroethane (HFA 134a) and/or I,1,1,2,3,3,3-heptafluoropropane (HFA 227).

In some embodiments, any of the pressurized fluid containers described herein can contain a propellant including chlorordifluoromethane ($CHClF_2$), 1-chloro-1,2,2,-trifluoroethethylene ($C_2CFIF_3$), ethyl fluoride ($C_2H_5F$), or the like.

In some embodiments, any of the pressurized fluid containers described herein can contain a propellant formulated from liquefied bis(difluoromethyl)ether and gaseous carbon dioxide. In other embodiments, any of the pressurized fluid containers described herein can contain propellants such as dinitrogen monoxide, hydrocarbons and fluorocarbons or liquid carriers (e.g., ethanol, perchloroethylene, trichloroethylene, acetone, amyl acetate, water and the like).

In some embodiments, any of the pressurized fluid containers described herein can contain a propellant formulated to have a suitable vapor pressure at or near room temperature. In this manner, the pressure used to non-manually actuate the medical injector can be controlled based on the propellant formulation. Moreover, selecting a propellant formulation that produces the desired pressure upon release limits the need for pressure amplification devices. In some embodiments, any of the pressurized fluid containers described herein can contain a propellant formulated to have a vapor pressure of approximately 270 p.s.i. at approximately 68° F. Such a propellant formulation can include, for example, a mixture of trifluoromethane (HFC-23) and difluoromethane (HFC-32). In some embodiments, any of the pressurized fluid containers described herein can contain a propellant formulated to have a vapor pressure of approximately 245 p.s.i. at approximately 68° F. Such a propellant formulation can include, for example, a mixture of trifluoromethane (HFC-23) and pentafluoroethane (HFC-32). In some embodiments, any of the pressurized fluid containers described herein can contain a propellant formulated to have a vapor pressure of approximately 215 p.s.i. at approximately 68° F. Such a propellant formulation can include, for example, trifluoromethane (HFC-23). In some embodiments, any of the pressurized fluid containers described herein can contain a propellant formulated to have a vapor pressure of approximately 200 p.s.i. at approximately 68° F. Such a propellant formulation can include, for example, Suva® 410A, produced by DuPont. In some embodiments, any of the pressurized fluid containers described herein can contain a propellant formulated to have a vapor pressure of between approximately 175 p.s.i. and 188 p.s.i. at approximately 68° F. Such a propellant formulation can include, for example, Suva® 125, produced by DuPont. In some embodiments, any of the pressurized fluid containers described herein can contain a propellant formulated to have a vapor pressure of approximately 75 p.s.i. at approximately 70° F. Such a propellant formulation can include, for example, HFA-134a.

In some embodiments, a propellant can include a single propellant, such as HCFC-141b or neopentane. In other embodiments, however, propellant blends may be employed. For example, a propellant blend may be prepared to reduce the rate of diffusion of the mixture across a barrier and/or to reduce any potential combustion hazard associated with the selected propellant. Propellant blends may include, for example, neopentane+$O_2$, neopentane+$N_2$, neopentane+$O_2$+$N_2$, neopentane+$CO_2$. Propellant blends including noble gases such as Ar, Xe and He may be prepared, for example to increase the vapor pressure of the mixture. Propellant blends can allow for the manufacture of compact constant pressure-based disposable pressure sources with pressure ranges up to >250 p.s.i. from a compact disposable cartridge. Specifically tailored propellant cartridges can be made to provide a range of useful constant pressures to accommodate the medicament viscosity and flow characteristics (e.g., flow rate through the needle) desired during the injection event.

In some embodiments, for example, a propellant blend can include $CO_2$, $N_2O$, $N_2$ and/or ethanol. In some embodiments, a propellant blend can include a mixture HFA 134a and $CO_2$, HFA 134a and $N_2O$, HFA 134a and $N_2$. In some embodiments, a propellant blend can include any suitable HFA formulation, any one or more of $CO_2$, $N_2O$, $N_2$, and ethanol.

Although the medical injectors are shown and described above as including a single pressurized fluid container, in some embodiments, a kit can include a medical injector and a set of pressurized fluid containers. For example, in some embodiments, a kit can include a medical injector similar to the medical injector 300 shown and described above, and a set of actuator assemblies, similar to the actuator assembly 350 shown and described above. Each actuator assembly in the kit can include a pressurized fluid container (similar to the pressurized fluid container 351) having a different propellant formulation from the other actuator assemblies in the kit. In this manner, a kit can include a set of actuator assemblies configured to produce a pressurized fluid having a range of different pressures. Thus, a user can select the appropriate actuator assembly based on the procedure to be performed.

For example, in some embodiments, a kit can include a first actuator assembly having a propellant formulation configured to produce 75 p.s.i., a second actuator assembly having a propellant formulation configured to produce 100 p.s.i., a third actuator assembly having a propellant formulation configured to produce 150 p.s.i., and a fourth actuator assembly having a propellant formulation configured to produce 250 p.s.i. The different actuator assemblies can, for example, be color-coded or otherwise labeled to indicate the pressure that can be produced by the propellant contained therein.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Although the medical injector 300 is shown and described above as including an actuator assembly 350 having a pre-filled pressurized fluid container 351, in other embodiments, a pressurized fluid container can be configured to filled by the user prior to injection and/or refilled for multiple uses. For example, in some embodiments, a kit can include an actuator assembly configured to be coupled to a medicament container and a source of pressurized fluid. The actuator assembly can have an opening or valve such that the user can convey a pressurized fluid from the source of pressurized fluid into the actuator assembly prior to using the actuator assembly to non-manually actuate a medical injector. In this manner, the user can fill and/or refill the actuator assembly in a manner to obtain a desired pressure (e.g., by filling and/or refilling with a desired mixture of propellant).

Although the medical injectors are shown and described above as including a pressurized fluid container, in other embodiments, a medical injector can include any suitable form of stored energy and/or a mechanism configured to convert energy from one form to another. Similarly stated, in some embodiments, a medical injector can include any suitable energy source to non-manually inject a medicament (i.e., to inject a medicament without the user producing the energy used for the injection). For example, in some embodiments an energy source can include a source of stored electrical energy (e.g., a battery), a source of chemical energy (e.g., products that react to produce energy), and/or a source of mechanical energy (e.g., a spring). In other embodiments, an energy source can include a mechanism configured to convert electrical potential energy to a kinetic energy. For example, in some embodiments, an energy source can include an electric motor (e.g., a stepper motor) configured to receive electrical energy (from a battery or from an AC power source) and convert the electrical energy into a kinetic energy to move a piston.

Although the medicament containers are shown and described above as including a piston, in other embodiments, a medicament container can be devoid of a piston. For example, in some embodiments, a medical injector can include a medicament container devoid of a piston, and can include a source of pressurized fluid. The dermal filler contained within the medicament container can have a high viscosity such that it will not readily mix with the pressurized fluid. Accordingly, to actuate the injector, the pressurized fluid is conveyed into the medicament container and into direct contact with the dermal filler to be injected, thereby moving the dermal filler within the medicament container.

Although the openings 376 of the valve stem 370 are shown above as having a substantially square cross-sectional shape (see e.g., FIG. 7), in other embodiments, the valve stem 370 can define flow openings having any suitable cross-sectional shape. As shown in FIG. 9, when the medical injector 300 is in the second configuration, a portion of the flow openings 376 are uncovered thereby allowing the pressurized fluid to be conveyed from the pressurized flow container 351. Thus, the uncovered portion of the flow openings 376 defines a flow area through which the pressurized fluid can flow. According, the cross-sectional shape of the openings 376 can produce a predetermined flow area as a function of the linear displacement of the actuator assembly 350. Similarly stated, the cross-sectional shape of the openings 376 can produce a predetermined flow area as a function of the amount of the flow openings 376 that is uncovered during actuation of the medical injector. In some embodiments, for example, the flow openings 376 can have a substantially circular cross-sectional shape. In other embodiments, the flow openings 376 can have a substantially rectangular cross-sectional shape such that the long side of the rectangular shape extends along the longitudinal axis of the medicament container 310.

Although various embodiments have been described as having particular features and/or combinations of components, other embodiments are possible having a combination of any features and/or components from any of embodiments where appropriate. For example, in some embodiments, any of the medical injectors described herein (e.g., a medical injector similar to the medical injector 100) can include a finger grip similar to the finger grip 216 show and described above with respect to the medical injector 200.

In some embodiments, a medical injector can include a first regulator assembly configured to regulate the flow of a pressurized fluid into a medicament container (e.g., similar to the regulator assembly 360) and a second regulator assembly configured restrict a medicament flow path (e.g., similar to the regulator assembly 760).

The invention claimed is:

1. An apparatus, comprising:
a medicament container having a distal end portion and a proximal end portion, the distal end portion configured to be coupled to a needle;
a piston movably disposed within the medicament container such that the medicament container is divided into a first internal portion and a second internal portion, the first internal portion configured to contain a medicament; and
an actuator assembly coupled to the proximal end portion of the medicament container, the actuator assembly having a pressurized fluid container, a regulator and a bias member,
the pressurized fluid container configured to move relative to the medicament container between a first position and a second position, the regulator configured to fluidically couple the pressurized fluid container and the second internal portion of the medicament container when the pressurized fluid container is in the second position, the bias member configured to bias the pressurized fluid container in the first position.

2. The apparatus of claim 1, wherein the pressurized fluid container is configured to move relative to the medicament container along a longitudinal axis of the medicament container from the first position to the second position and from the second position to the first position.

3. The apparatus of claim 1, wherein the pressurized fluid container is configured to move a distance of less than approximately 13 mm from the first position to the second position and from the second position to the first position.

4. The apparatus of claim 1, wherein the regulator is configured to regulate a flow rate of a fluid from the pressurized fluid container into the second internal portion of the medicament container when the pressurized fluid container is moved from the first position to the second position.

5. The apparatus of claim 1, wherein the regulator is configured to selectively place the second internal portion of the medicament container in fluid communication with a region outside of the medicament container when the pressurized fluid container is in the first position.

6. The apparatus of claim 1, wherein the regulator includes a valve stem defining a flow opening having a non-circular cross-sectional shape.

7. The apparatus of claim 1, wherein the pressurized fluid container includes a fluid having a vapor pressure of at least approximately 517 kilopascals at 21 degrees Celsius.

8. The apparatus of claim 1, wherein the pressurized fluid container includes a fluid having a vapor pressure of between approximately 517 kilopascals and approximately 1723 kilopascals at 21 degrees Celsius.

9. The apparatus of claim 1, wherein the pressurized fluid container includes a mixture of trifluoromethane (HFC-23) and pentafluoroethane (HFC-32) such that the mixture has a fluid having a vapor pressure of approximately 1.7 Megapascals at 21 degrees Celsius.

10. The apparatus of claim 1, wherein the pressurized fluid container includes a mixture of any one of a hydrofluoroalkane, $CO_2$, $N_2O$, $N_2$ and ethanol.

11. The apparatus of claim 1, wherein:
a central portion of the medicament container includes a first protrusion and a second protrusion, the first protrusion and the second protrusion collectively configured to be grasped by a first finger and a second finger of a user when the pressurized fluid container is moved from the first position to the second position; and
a proximal end of the actuator assembly defines a recess configured to receive a portion of a thumb of the user such that the pressurized fluid container can be moved from the first position to the second position by moving the proximal end of the actuator assembly via the thumb relative to the central portion of the medicament container when the first protrusion and the second protrusion are grasped by the first finger and the second finger.

12. The apparatus of claim 1, wherein the regulator includes a valve stem and a valve seal, the valve stem defining a flow opening, the valve seal configured to be disposed about the flow opening when the pressurized fluid container is in the first position, the valve seal and the bias member being monolithically constructed.

13. An apparatus, comprising:
a medicament container having a distal end portion, a proximal end portion, and a central portion therebetween, the distal end portion configured to be coupled to a needle, the central portion including a finger grip configured to engage a first finger and a second finger of a user;
a piston movably disposed within the medicament container such that the medicament container is divided into a first internal portion and a second internal portion, the first internal portion configured to contain a medicament;
a pressurized fluid container coupled to the proximal end portion of the medicament container, the pressurized fluid container configured to be moved relative to the medicament container from a first position to a second position when the finger grip is engaged by the first finger and the second finger and a proximal end of the pressurized fluid container is moved relative to the finger grip via a thumb of the user; and
a regulator including a valve stem and a valve seal, the valve stem defining a flow opening, the valve seal coupled to the pressurized fluid container such that the valve seal moves with the pressurized fluid container,
wherein the valve seal is configured to be disposed about the flow opening when the pressurized fluid container is in the first position, and the regulator is configured to fluidically couple the pressurized fluid container and the second internal portion of the medicament container when the pressurized fluid container is in the second position.

14. The apparatus of claim 13, wherein the pressurized fluid container is configured to move relative to the medicament container along a longitudinal axis of the medicament container a distance of less than approximately 13 mm from the first position to the second position and from the second position to the first position.

15. The apparatus of claim 13, wherein the regulator is configured to regulate a flow rate of a fluid from the pressurized fluid container into the second internal portion of the medicament container when the pressurized fluid container is moved from the first position to the second position.

16. The apparatus of claim 13, further comprising:
a bias member configured to bias the pressurized fluid container in the first position.

17. The apparatus of claim 16, wherein the valve seal and the bias member are monolithically constructed, and wherein movement of the pressurized fluid container from the first position to the second position also moves the valve seal against the bias of the bias member.

18. The apparatus of claim 16, wherein when the pressurized fluid container is moved against the bias of the bias member to the second position, the regulator fluidically couples the pressurized fluid container and the second internal portion of the medicament container automatically and continually until the bias member returns the pressurized fluid container to the first position.

19. The apparatus of claim 12, wherein the pressurized fluid container is coupled to the valve seal such that movement of the pressurized fluid container from the first position to the second position also moves the valve seal against the bias of the bias member.

20. The apparatus of claim 1, wherein when the pressurized fluid container is moved against the bias of the bias member to the second position, the regulator fluidically couples the pressurized fluid container and the second internal portion of the medicament container automatically and continually until the bias member returns the pressurized fluid container to the first position.

* * * * *